(12) United States Patent
Takeuchi et al.

(10) Patent No.: US 8,658,623 B2
(45) Date of Patent: Feb. 25, 2014

(54) SUBSTITUTED BICYCLIC METHYL AMINE DERIVATIVES AS SPHINGOSINE-1 PHOSPHATE RECEPTORS MODULATORS

(71) Applicant: Allergan, Inc., Irvine, CA (US)

(72) Inventors: Janet A. Takeuchi, Anaheim, CA (US); Ling Li, Irvine, CA (US); Wha-Bin Im, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/943,166

(22) Filed: Jul. 16, 2013

(65) Prior Publication Data

US 2013/0338109 A1 Dec. 19, 2013

Related U.S. Application Data

(62) Division of application No. 13/445,991, filed on Apr. 13, 2012, now Pat. No. 8,513,418.

(60) Provisional application No. 61/476,367, filed on Apr. 18, 2011.

(51) Int. Cl.

| | |
|---|---|
| *A61K 31/675* | (2006.01) |
| *A61K 31/47* | (2006.01) |
| *A61K 31/661* | (2006.01) |
| *A61K 31/662* | (2006.01) |
| *A61P 1/00* | (2006.01) |
| *A61P 5/00* | (2006.01) |
| *A61P 9/10* | (2006.01) |
| *A61P 11/00* | (2006.01) |
| *A61P 13/12* | (2006.01) |
| *A61P 17/00* | (2006.01) |
| *A61P 17/02* | (2006.01) |
| *A61P 17/06* | (2006.01) |
| *A61P 19/10* | (2006.01) |
| *A61P 21/04* | (2006.01) |
| *A61P 25/00* | (2006.01) |
| *A61P 25/28* | (2006.01) |
| *A61P 27/02* | (2006.01) |
| *A61P 27/06* | (2006.01) |
| *A61P 29/00* | (2006.01) |
| *A61P 31/00* | (2006.01) |
| *A61P 35/04* | (2006.01) |
| *A61P 37/06* | (2006.01) |
| *A61P 37/08* | (2006.01) |

(52) U.S. Cl.
USPC ......... 514/82; 514/114; 514/210.18; 514/311

(58) Field of Classification Search
None
See application file for complete search history.

(56) References Cited

U.S. PATENT DOCUMENTS

| | | |
|---|---|---|
| 2005/0020837 A1 | 1/2005 | Doherty et al. |
| 2011/0105432 A1 | 5/2011 | Habashita et al. |
| 2011/0230463 A1 | 9/2011 | Harada et al. |

FOREIGN PATENT DOCUMENTS

| | | |
|---|---|---|
| WO | 2003-061567 | 7/2003 |
| WO | 2003-062248 | 7/2003 |
| WO | 2005-000833 | 1/2005 |

OTHER PUBLICATIONS

Cross, LC, Rules for the Nomenclature of Organic Chemistry Section E: Sterochemistry, Pure & Appl. Chem., 1976, 11-30, 45.
Hale, Jeffrey J., Potent S1P receptor agonists replicate the pharmacologic actions of the novel immune modulator FTY720, Bioorganic & Medicinal Chemistry Letters, 2004, 3351-3355, 14, US.
Hale, Jeffrey J., Selecting against SIP3 enhances the acute cardiovascular tolerability of 3-(N-benzyl) aminopropylphosphonic acid SIP receptor agonists, Bioorganic & Medicinal Chemistry Letters, 2004, 3501-3505, 14, US.
Stahl, Heinrich et al, Handbook of Pharmaceutical Salts, Verlag Helvetica Chimica Acta—Zurich, 2002, 329-345.
Patent Cooperation Treaty, Notification of Transmittal of the International Search Report and the Written Opinion of the International Searching Authority, or the Declaration, Form PCT/ISA/220, Int. App. No. PCT/US2012/033459, Jun. 22, 2012.

*Primary Examiner* — Janet L Andres
*Assistant Examiner* — Timothy R Rozof
(74) *Attorney, Agent, or Firm* — Doina G. Ene

(57) ABSTRACT

The present invention relates to novel substituted bicyclic methyl amine derivatives which are useful as sphingosine-1-phosphate receptors modulators and useful for treating a wide variety of disorders associated with modulation of sphingosine-1-phosphate receptors.

8 Claims, 1 Drawing Sheet

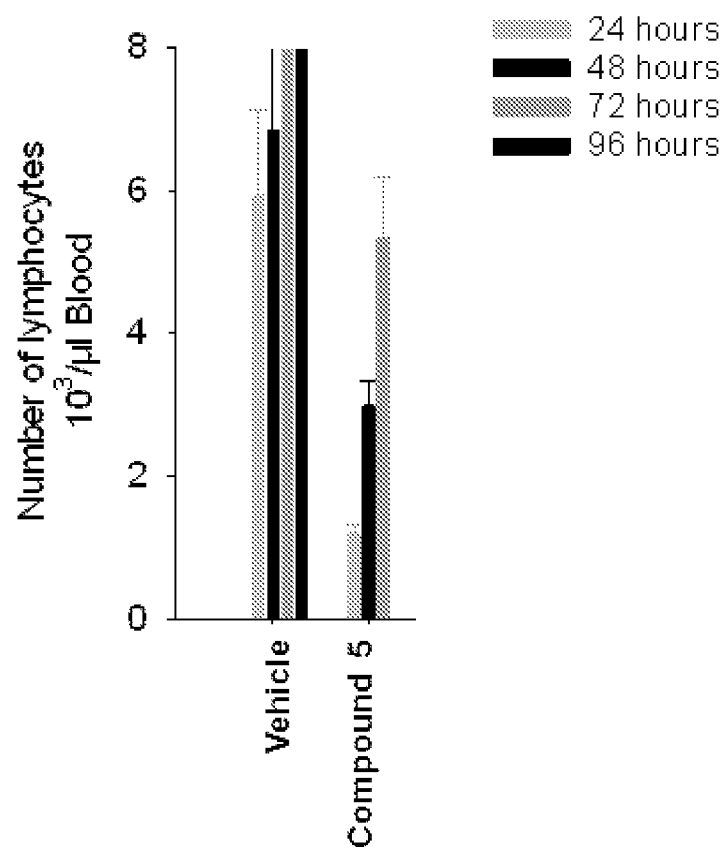

SUBSTITUTED BICYCLIC METHYL AMINE DERIVATIVES AS SPHINGOSINE-1 PHOSPHATE RECEPTORS MODULATORS

RELATED APPLICATION

This application is a divisional application of U.S. Non-Provisional patent application Ser. No. 13/445,991, filed Apr. 13, 2012, which claims the benefit of U.S. Provisional Patent Application Ser. No. 61/476,367 filed Apr. 18, 2011, all of which are incorporated herein by reference in their entirety.

FIELD OF THE INVENTION

The present invention relates to novel substituted bicyclic methyl amine derivatives, processes for preparing them, pharmaceutical compositions containing them and their use as pharmaceuticals as modulators of sphingosine-1-phosphate receptors. The invention relates specifically to the use of these compounds and their pharmaceutical compositions to treat disorders associated with sphingosine-1-phosphate (S1P) receptor modulation.

BACKGROUND OF THE INVENTION

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular diseases. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

SUMMARY OF THE INVENTION

We have now discovered a group of novel compounds which are potent and selective sphingosine-1-phosphate modulators. As such, the compounds described herein are useful in treating a wide variety of disorders associated with modulation of sphingosine-1-phosphate receptors. The term "modulator" as used herein, includes but is not limited to: receptor agonist, antagonist, inverse agonist, inverse antagonist, partial agonist, partial antagonist.

This invention describes compounds of Formula I, which have sphingosine-1-phosphate receptor biological activity. The compounds in accordance with the present invention are thus of use in medicine, for example in the treatment of humans with diseases and conditions that are alleviated by S1P modulation.

In one aspect, the invention provides a compound having Formula I or a pharmaceutically acceptable salt thereof or stereoisomeric forms thereof, or the geometrical isomers, enantiomers, diastereoisomers, tautomers, zwitterions and pharmaceutically acceptable salts thereof:

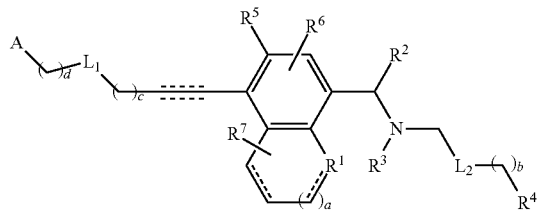

Formula I wherein:

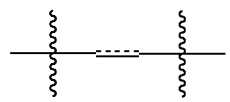

represents a single bond

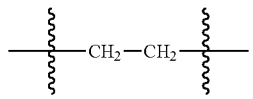

or a double bond

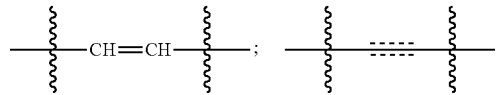

represents a single bond

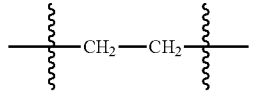

or a double bond

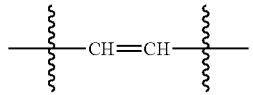

or a triple bond

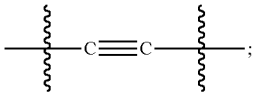

A is substituted or unsubstituted $C_{6-10}$ aryl, substituted or unsubstituted heterocycle substituted or unsubstituted $C_{5-8}$ cycloalkyl, substituted or unsubstituted $C_{5-8}$ cycloalkenyl, or H;

$R^2$ is H, halogen, $-OC_{1-3}$ alkyl, substituted or unsubstituted $C_{1-3}$ alkyl, CN, $C(O)R^8$, $NR^9R^{10}$ or hydroxyl;

$R^3$ is H, halogen, substituted or unsubstituted $C_{1-3}$ alkyl, $C(O)R^8$ or hydroxyl;

$R^4$ is $OPO_3H_2$, carboxylic acid, $PO_3H_2$, $C_{1-6}$ alkyl, $-S(O)_2H$, $-P(O)MeOH$, $-P(O)(H)OH$ or $OR^{11}$;

$R^5$ is H, halogen, $-OC_{1-3}$ alkyl, substituted or unsubstituted $C_{1-3}$ alkyl, CN, $C(O)R^8$, $NR^9R^{10}$ or hydroxyl;

$R^6$ is H, halogen, $-OC_{1-3}$ alkyl, substituted or unsubstituted $C_{1-3}$ alkyl, CN, $C(O)R^8$, $NR^9R^{10}$ or hydroxyl;

$R^7$ is H, halogen, $-OC_{1-3}$ alkyl, substituted or unsubstituted $C_{1-3}$ alkyl, CN, $C(O)R^8$, $NR^9R^{10}$ or hydroxyl;

$R^8$ is H, $OR^{11}$ or substituted or unsubstituted $C_{1-3}$ alkyl;

$R^9$ is H or substituted or unsubstituted $C_{1-3}$ alkyl;

$R^{10}$ is H or substituted or unsubstituted $C_{1-3}$ alkyl;

$R^{11}$ is H or substituted or unsubstituted $C_{1-3}$ alkyl;

$L^1$ is O, S, NH or $CH_2$;

$L^2$ is O, S, NH or $CH_2$;

a is 0 or 1;

b is 0, 1, 2 or 3;

c is 1, 2, 3 or 4;

d is 1, 2 or 3; with the provisos when a is 1 then

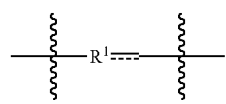

represents

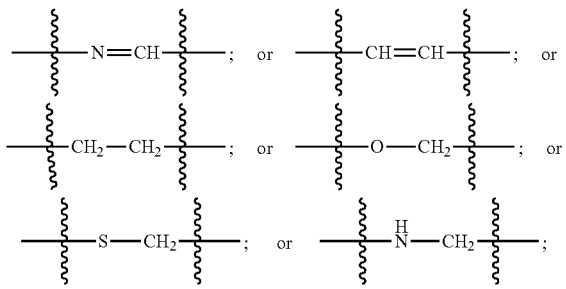

and when a is 0 then $R^1$ is O, S, NH, or $CH_2$.

In another embodiment, the invention provides a compound having Formula I wherein:

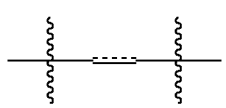

represents a single bond

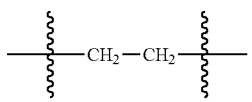 [SMILES: *CC*]

or a double bond

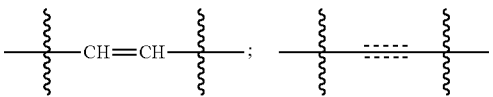

represents a single bond

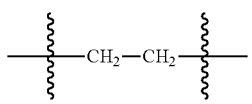 [SMILES: *CC*]

or a double bond

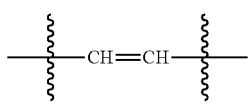

or a triple bond

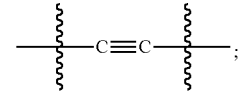 [SMILES: *C#C*]

A is substituted or unsubstituted $C_{6-10}$ aryl, substituted or unsubstituted heterocycle substituted or unsubstituted $C_{5-8}$ cycloalkyl, substituted or unsubstituted $C_{5-8}$ cycloalkenyl, or H;

$R^2$ is H, halogen, $-OC_{1-3}$ alkyl, substituted or unsubstituted $C_{1-3}$ alkyl, CN, $C(O)R^8$, $NR^9R^{10}$ or hydroxyl;

$R^3$ is H, halogen, substituted or unsubstituted $C_{1-3}$ alkyl, $C(O)R^8$ or hydroxyl;

$R^4$ is $OPO_3H_2$, carboxylic acid, $PO_3H_2$, $C_{1-6}$ alkyl, $-S(O)_2H$, $-P(O)MeOH$, $-P(O)(H)OH$ or $OR^{11}$;

$R^5$ is H, halogen, $-OC_{1-3}$ alkyl, substituted or unsubstituted $C_{1-3}$ alkyl, CN, $C(O)R^8$, $NR^9R^{10}$ or hydroxyl;

$R^6$ is H, halogen, $-OC_{1-3}$ alkyl, substituted or unsubstituted $C_{1-3}$ alkyl, CN, $C(O)R^8$, $NR^9R^{10}$ or hydroxyl;

$R^7$ is H, halogen, $-OC_{1-3}$ alkyl, substituted or unsubstituted $C_{1-3}$ alkyl, CN, $C(O)R^8$, $NR^9R^{10}$ or hydroxyl;

$R^8$ is H, $OR^{11}$ or substituted or unsubstituted $C_{1-3}$ alkyl;

$R^9$ is H or substituted or unsubstituted $C_{1-3}$ alkyl;

$R^{10}$ is H or substituted or unsubstituted $C_{1-3}$ alkyl;

$R^{11}$ is H or substituted or unsubstituted $C_{1-3}$ alkyl;

$L^1$ is O, S, NH or $CH_2$;

$L^2$ is O, S, NH or $CH_2$;

a is 1;

b is 0, 1, 2 or 3;

c is 1, 2, 3 or 4;

d is 1, 2 or 3; and represents

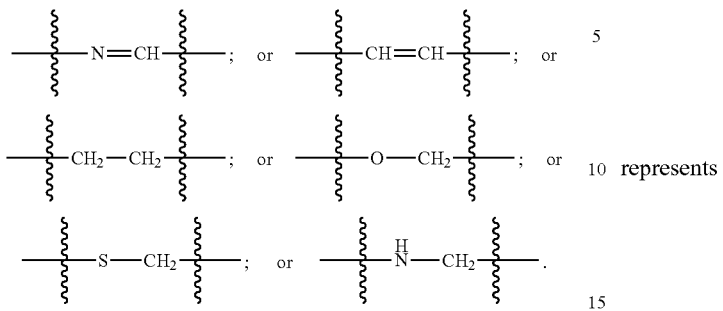

In another embodiment, the invention provides a compound having Formula I wherein:

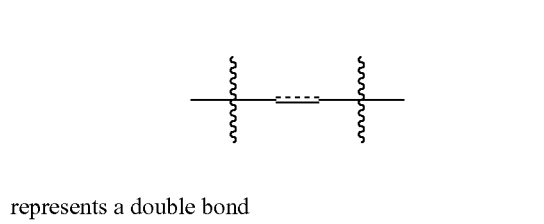

represents a double bond

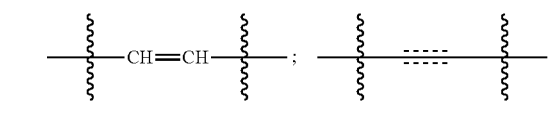

represents a single bond

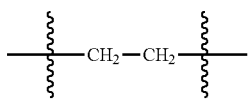

or a triple bond

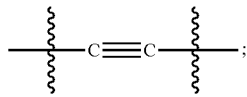 [SMILES: *C#C*]

A is substituted or unsubstituted $C_{6-10}$ aryl or H;
$R^2$ is H or substituted or unsubstituted $C_{1-3}$ alkyl;
$R^3$ is H;
$R^4$ is $PO_3H_2$, $OPO_3H_2$ or $OR^{11}$;
$R^5$ is H;
$R^6$ is H;
$R^7$ is H;
$R^{11}$ is H or substituted or unsubstituted $C_{1-3}$ alkyl;
$L^1$ is $CH_2$;
$L^2$ is $CH_2$;
a is 1;
b is 1;
c is 1, 2, 3 or 4;
d is 1, 2 or 3; and

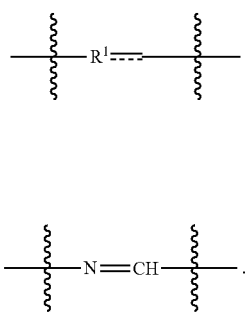

represents

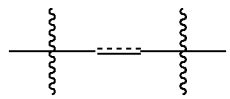

In another embodiment, the invention provides a compound having Formula I wherein:

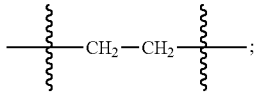

represents a double bond

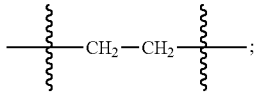

represents a triple bond

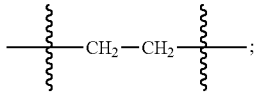

A is substituted or unsubstituted phenyl or H;
$R^2$ is H;
$R^3$ is H;
$R^4$ is $OPO_3H_2$, $OPO_3H_2$, or $OR^{11}$;
$R^5$ is H;
$R^6$ is H;
$R^7$ is H;
$R^{11}$ is H;
$L^1$ is $CH_2$;
$L^2$ is $CH_2$;
a is 1;
b is 1;
c is 1, 2, 3 or 4;
d is 1, 2 or 3; and

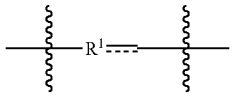

represents

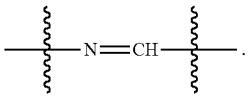 [SMILES: *C=N*]

In another embodiment, the invention provides a compound having Formula I wherein:

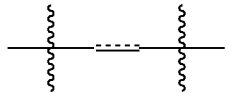

represents a double bond

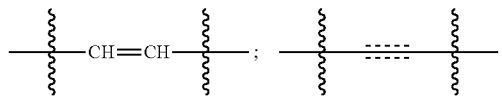

represents a triple bond

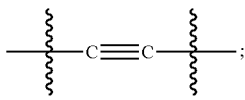 [SMILES: *C#C*]

A is substituted or unsubstituted phenyl or H;
$R^2$ is H or substituted or unsubstituted $C_{1-3}$ alkyl;
$R^3$ is H;
$R^4$ is $OPO_3H_2$;
$R^5$ is H;
$R^6$ is H;
$R^7$ is H;
$L^1$ is $CH_2$;
$L^2$ is $CH_2$;
a is 1;
b is 1;
c is 1, 2 or 4;
d is 1, 2 or 3; and

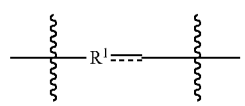

represents

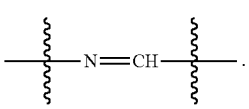 [SMILES: *C=N*]

In another embodiment, the invention provides a compound having Formula I wherein:

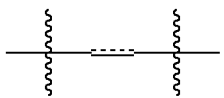

represents a double bond

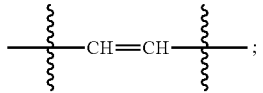

represents a triple bond

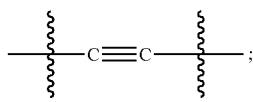 [SMILES: *C#C*]

A is substituted or unsubstituted phenyl;
$R^2$ is H or substituted or unsubstituted $C_{1-3}$ alkyl;
$R^3$ is H;
$R^4$ is $OPO_3H_2$;
$R^5$ is H;
$R^6$ is H;
$R^7$ is H;
$L^1$ is $CH_2$;
$L^2$ is $CH_2$;
a is 1;
b is 1;
c is 1 or 2;
d is 1, 2 or 3; and

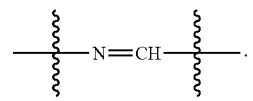

represents

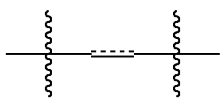

In another embodiment, the invention provides a compound having Formula I wherein:

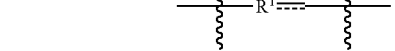

represents a double bond

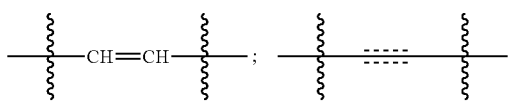

represents a triple bond

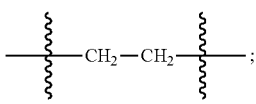 [SMILES: *CC*]

A is substituted or unsubstituted phenyl;
$R^2$ is H;
$R^3$ is H;
$R^4$ is $OPO_3H_2$, $OPO_3H_2$, or $OR^{11}$;
$R^5$ is H;
$R^6$ is H;
$R^7$ is H;
$R^{11}$ is H;
$L^1$ is $CH_2$;
$L^2$ is $CH_2$;
a is 1;
b is 1;
c is 2 or 3;
d is 2 or 3; and

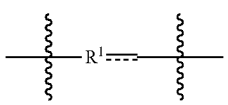

represents

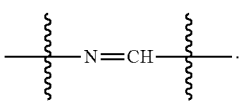

In another embodiment, the invention provides a compound having Formula I wherein:

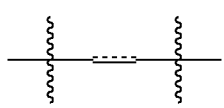

represents a single bond

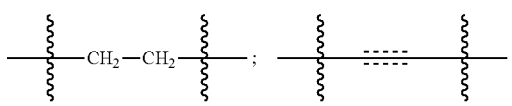

represents a triple bond

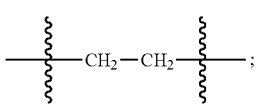

A is substituted phenyl;
$R^2$ is H;
$R^3$ is H;
$R^4$ is, $PO_3H_2$;
$R^5$ is H;
$R^6$ is H;
$R^7$ is H;
$L^1$ is $CH_2$;
$L^2$ is $CH_2$;
a is 1;
b is 1;
c is 2;
d is 1; and

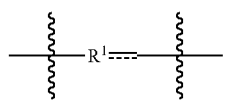

represents

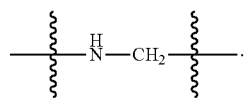 [SMILES: *CN*]

The term "alkyl", as used herein, refers to saturated, monovalent or divalent hydrocarbon moieties having linear or branched moieties or combinations thereof and containing 1 to 10 carbon atoms. One methylene (—$CH_2$—) group, of the alkyl can be replaced by oxygen, sulfur, sulfoxide, nitrogen, carbonyl, carboxyl, sulfonyl, or by a divalent $C_{3-10}$ cycloalkyl. Alkyl groups can be substituted by halogen, hydroxyl, cycloalkyl, amino, heterocycles, carboxylic acid, phosphonic acid groups, sulphonic acid groups, phosphoric acid.

The term "cycloalkyl", as used herein, refers to a monovalent or divalent group of 3 to 10 carbon atoms derived from a saturated cyclic hydrocarbon. Cycloalkyl groups can be monocyclic or polycyclic. Cycloalkyl can be substituted by $C_{1-3}$ alkyl groups or halogens.

The term "halogen", as used herein, refers to an atom of chlorine, bromine, fluorine, iodine.

The term "heterocycle" as used herein, refers to a 3 to 10 membered ring, which can be aromatic or non-aromatic, saturated or non-saturated, containing at least one heteroatom selected form O or N or S or combinations of at least two thereof, interrupting the carbocyclic ring structure. The heterocyclic ring can be saturated or non-saturated. The heterocyclic ring can be interrupted by a C=O; the S heteroatom can be oxidized. Heterocycles can be monocyclic or polycyclic. Heterocyclic ring moieties can be substituted by hydroxyl, $C_{1-3}$ alkyl or halogens.

The term "aryl" as used herein, refers to an organic moiety derived from an aromatic hydrocarbon consisting of a ring containing 6 to 10 carbon atoms by removal of one hydrogen, which can be substituted by halogen atoms, —$OC_{1-3}$ alkyl, $C_{1-3}$ alkyl, nitrile, $C(O)C_{1-3}$ alkyl, amino or hydroxyl groups.

The term "hydroxyl" as used herein, represents a group of formula "—OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

The term "nitrile", as used herein, represents a group of formula "—CN".

The term "sulfoxide" as used herein, represents a group of formula "—S(O)".

The term "carbonyl" as used herein, represents a group of formula "—C(O)".

The term "carboxyl" as used herein, represents a group of formula "—(CO)O—".

The term "sulfonyl" as used herein, represents a group of formula —SO$_2$".

The term "amino" as used herein, represents a group of formula "—NR$^x$R$^y$", wherein R$^x$ and R$^y$ are independently selected from: hydrogen, alkyl, aryl, heterocycle as defined above.

The term "carboxylic acid" as used herein, represents a group of formula "—COOH".

The term "phosphonic acid" as used herein, represents a group of formula "—P(O)(OH)$_2$".

The term "sulphonic acid" as used herein, represents a group of formula "—SO$_2$(OH)".

The term "phosphoric acid" as used herein, represents a group of formula "—OP(O)(OH)$_2$".

Compounds of the invention are:

(3-{[(5-decylquinolin-8-yl)methyl]amino}propyl)phosphonic acid;

(3-{[(5-dec-1-yn-1-ylquinolin-8-yl)methyl]amino}propyl) phosphonic acid;

[3-({[5-(7-phenylhept-1-yn-1-yl)quinolin-8-yl] methyl}amino)propyl]phosphonic acid;

[3-({[5-(6-phenylhex-1-yn-1-yl)quinolin-8-yl] methyl}amino)propyl]phosphonic acid;

[3-({[5-(7-phenylheptyl)quinolin-8-yl]methyl}amino)propyl]phosphonic acid;

(3-{[(5-dec-1-yn-1-ylquinolin-8-yl)methyl]amino}butyl) phosphonic acid;

[3-({[5-(6-phenylhexyl)quinolin-8-yl]methyl}amino)propyl]phosphonic acid;

[3-({[5-(5-phenylpent-1-yn-1-yl)quinolin-8-yl] methyl}amino)propyl]phosphonic acid;

[3-({[5-(5-phenylpentyl)quinolin-8-yl]methyl}amino)propyl]phosphonic acid;

2-({[5-(6-phenylhexyl)quinolin-8-yl]methyl}amino)ethanol;

2-({[5-(6-phenylhexyl)quinolin-8-yl]methyl}amino)ethyl dihydrogen phosphate;

{3-[({5-[6-(3-methoxyphenyl)hex-1-yn-1-yl]quinolin-8-yl}methyl)amino]propyl}phosphonic acid;

{3-[({5-[6-(3-methoxyphenyl)hexyl]quinolin-8-yl}methyl) amino]propyl}phosphonic acid;

{3-[({5-[6-(3-methoxyphenyl)hexyl]-5,6,7,8-tetrahydroquinolin-8-yl}methyl)amino]propyl}phosphonic acid;

{3-[({4-[(1E)dec-1-en-1-yl]-1-naphthyl}methyl)amino] propyl}phosphonic acid;

[3-({[4-(6-phenylhex-1-yn-1-yl)-1-naphthyl]methyl}amino) propyl]phosphonic acid;

2-({[4-(6-phenylhexyl)-1-naphthyl]methyl}amino)ethanol;

2-({[4-(6-phenylhexyl)-1-naphthyl]methyl}amino)ethyl dihydrogen phosphate;

[3-({[4-(6-phenylhexyl)-1-naphthyl]methyl}amino)propyl] phosphonic acid;

{3-[({4-[6-(3-methoxyphenyl)hex-1-yn-1-yl]-1-naphthyl}methyl)amino]propyl}phosphonic acid;

2-[({4-[6-(3-methoxyphenyl)hex-1-yn-1-yl]-1-naphthyl}methyl)amino]ethyl dihydrogen phosphate;

{3-[({4-[6-(3-methoxyphenyl)hexyl]-1-naphthyl}methyl) amino]propyl}phosphonic acid;

2-[({4-[6-(3-methoxyphenyl)hexyl]-1-naphthyl}methyl) amino]ethanol;

2-[({4-[6-(3-methoxyphenyl)hexyl]-1-naphthyl}methyl) amino]ethyl dihydrogen phosphate.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic, for example, a hydrohalic such as hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chemica Acta-Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahal & Camille G. Wermuth (Eds), Verlag Helvetica Chemica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P modulation: not limited to the treatment of diabetic retinopathy, other retinal degenerative conditions, dry eye, angiogenesis and wounds.

Therapeutic utilities of S1P modulators are ocular diseases, such as but not limited to: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases such as but not limited to: various inflammatory diseases, including acute lung injury, its prevention, sepsis, tumor metastasis, atherosclerosis, pulmonary edemas, and ventilation-induced lung injury; or autoimmune diseases and immunosuppression such as but not limited to: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation; or allergies and other inflammatory diseases such as but not limited to: urticaria, bronchial asthma, and other airway inflammations including pulmonary emphysema and chronic obstructive pulmonary diseases; or cardiac protection such as but not limited to: ischemia reperfusion injury and atherosclerosis; or wound healing such as but not limited to: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation such as but not limited to: treatment of osteoporosis and various bone fractures including hip and ankles; or anti-nociceptive activity such as but not limited to: visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular disease, wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases, various inflammatory diseases, including acute lung injury, its prevention, sepsis, tumor metastasis, atherosclerosis, pulmonary edemas, and ventilation-induced lung injury; or autoimmune diseases and immunosuppression, rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation; or allergies and other inflammatory diseases, urticaria, bronchial asthma, and other airway inflammations including pulmonary emphysema and chronic obstructive pulmonary diseases; or cardiac protection, ischemia reperfusion injury and atherosclerosis; or wound healing, scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation, treatment of osteoporosis and various bone fractures including hip and ankles; or anti-nociceptive activity, visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier therefor. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I.

The compounds of Formula I according to the invention can be prepared analogously to conventional methods as understood by the person skilled in the art of synthetic organic chemistry. The synthetic scheme set forth below, illustrates how compounds according to the invention can be made. Those skilled in the art will be able to routinely modify and/or adapt the following scheme to synthesize any compounds of the invention covered by Formula I.

A solution of 5-bromo-8-quinolinecarboxaldehyde reacts with the desired alkyne in the presence of triethylamine and 1,3-bis(diphenylphosphino)propane in DMF (10 mL) at 90° C. After cooling to RT, and extraction with ether the aldehyde intermediate is Purified by MPLC. The solution of aldehyde intermediate reacts with an aminoalkyl phosphonic acid and tetrabutylammonium hydroxide at 50° C. and with sodium cyanoborohydride. The final compound is purified by MPLC. The triple bond on the aldehyde intermediate can be saturated to the corresponding alkane in the presence of 10% palladium on carbon in ethyl acetate and a $H_2$ balloon with stirring at RT for 16 h.

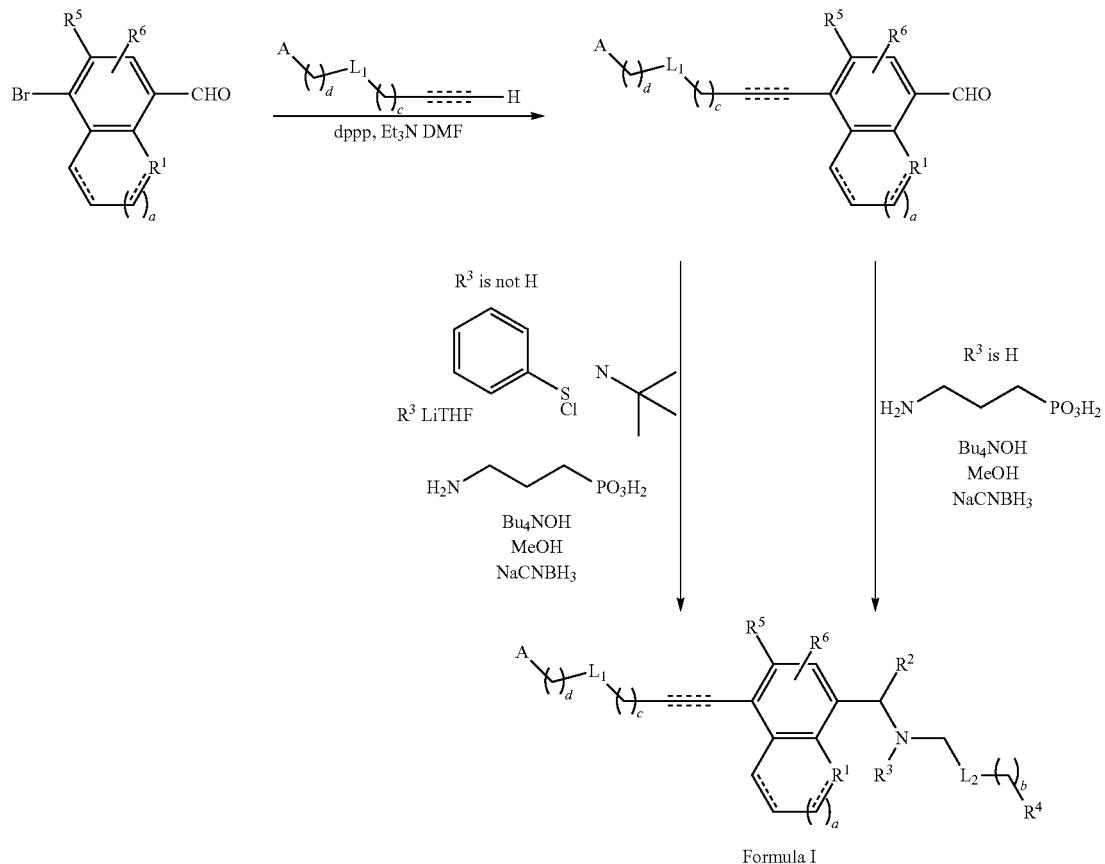

Trituration or column chromatography (methanol/ethyl acetate) gave the corresponding compound of Formula I.
dppp 1,3-Bis(diphenylphosphino)propane
Et$_3$N triethylamine
DMF N,N-dimethylformamide
NaCNBH$_3$ sodium cyanoborohydride
Bu$_4$NOH tetrabutylammonium hydroxide
To a solution of an appropriate terminal alkyne and a desired bromoquinolone aldehyde or bromonaphthyl aldehyde in DMF were added triethylamine and dppp. After heating to 90° C. with stirring for 2 h, the reaction mixture was cooled to room temperature, extracted with ether and washed with water and brine. The resulting coupled product may be either further reduced to the alkane aryl aldehyde or the alkyl substituted tetrahydroquinoline aldehyde. The compound of Formula I is obtained from reductive amination between the aryl aldehyde and the amine derivative.

BRIEF DESCRIPTION OF THE FIGURE

FIG. 1 shows that Compound 5 lowered lymphocyte count after 24 hours in a lymphopenia assay in mice, by measuring the in vivo blood lymphocyte depletion after dosing.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of hydrogen $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

The IUPAC names of the compounds mentioned in the examples were generated with ACD version 8.

Unless specified otherwise in the examples, characterization of the compounds is performed according to the following methods:

NMR spectra are recorded on 300 or 600 MHz Varian and acquired at room temperature. Chemical shifts are given in ppm referenced either to internal trimethylsilyl or to the residual solvent signal.

All the reagents, solvents, catalysts for which the synthesis is not described are purchased from chemical vendors such as Sigma Aldrich, Fluka, Bio-Blocks, Ryan Scientific, Syn Chem, Chem-Impex, Aces Pharma, however some known intermediates, for which the CAS registry number [CAS #] are mentioned, were prepared in-house following known procedures.

Usually the compounds of the invention were purified by flash column chromatography using a gradient solvent system of methanol/dichloromethane unless otherwise reported.

The following abbreviations are used in the examples:
DMF N,N-dimethylformamide
NaOH sodium hydroxide
CD$_3$OD deuterated methanol
HCl hydrochloric acid
CDCl$_3$ deuterated chloroform
DMSO-d$_6$ deuterated dimethyl sulfoxide
MPLC medium pressure liquid chromatography
THF tetrahydrofuran
RT room temperature
H$_2$ hydrogen
MeOH methanol
SiO$_2$ silicagel Those skilled in the art will be able to routinely modify and/or adapt the following schemes to synthesize any compound of the invention covered by Formula I.

Some compounds of this invention can generally be prepared in one step from commercially available literature starting materials.

EXAMPLE 1

Intermediate 1

1-(5-dec-1-yn-1-ylquinolin-8-yl)ethanone

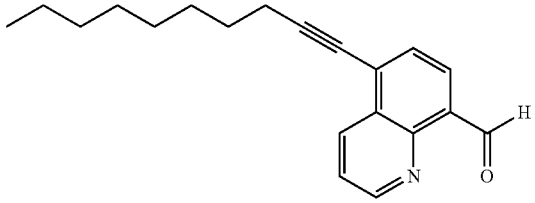 [SMILES: CCCCCCCCC#Cc1ccc(C=O)c2ncccc12]

A solution of 5-bromo-8-quinolinecarboxaldehyde (987 mL, 418 mmol), 1-decyne (1.05 mL, 5.85 mmol), triethylamine (2 mL) and 1,3-bis(diphenylphosphino)propane (dppp), (59 mg) in DMF (10 mL) was heated to 90° C. with stirring for 2 h. After cooling to RT, the reaction mixture was extracted with ether and washed with water and brine, dried over magnesium sulfate and concentrated. Purification by MPLC (35% ethyl acetate in hexanes) gave rise to 1.04 g of Intermediate 1 as yellow solid.

$^1$H NMR (600 MHz, CDCl$_3$) δ ppm 11.42 (d, J=0.88 Hz, 1 H), 9.09 (dd, J=4.25, 1.61 Hz, 1 H), 8.74 (dd, J=8.51, 1.47 Hz, 1 H), 8.28 (d, J=7.34 Hz, 1 H), 7.78 (d, J=7.63 Hz, 1 H), 7.59 (dd, J=8.51, 4.11 Hz, 1 H), 2.60 (t, J=7.19 Hz, 2 H), 01.72 (m, J=14.89, 7.37, 7.37 Hz, 2 H), 1.44-1.63 (m, 2 H), 1.19-1.44 (m, 8 H), 0.89 (t, J=7.00 Hz, 3 H).

Intermediates 2-6 were prepared from the corresponding aldehydes in a similar manner to the method described in Example 1 for Intermediate 1. The reactants used and the results are described below in Table 1.

TABLE 1

| Interm. No. | IUPAC name | Starting material | $^1$H NMR δ (ppm) for Compound |
|---|---|---|---|
| 2 | 5-(7-phenylhept-1-yn-1-yl)quinoline-8-carbaldehyde | 6-heptyn-1-yl-benzene [CAS56293-02-8] | $^1$H NMR (600 MHz, CDCl$_3$) δ 11.42 (s, 1H), 9.06 (dd, J = 1.91, 3.96 Hz, 1H), 8.67 (dd, J = 1.76, 8.51 Hz, 1H), 8.25 (dd, J = 1.17, 7.63 Hz, 1H), 7.73 (d, J = 7.34 Hz, 1H), 7.55 (td, J = 1.91, 4.04 Hz, 1H), 7.11-7.28 (m, 5H), 2.67 (t, J = 7.78 Hz, 2H), 2.60 (t, J = 7.04 Hz, 2H), 1.67-1.82 (m, 4H), 1.53-1.63 (m, 2H) |

TABLE 1-continued

| Interm. No. | IUPAC name | Starting material | ¹H NMR δ (ppm) for Compound |
|---|---|---|---|
| 3 | 5-[6-(3-methoxyphenyl)hex-1-yn-1-yl]quinoline-8-carbaldehyde | 1-(-5-hexyn-1-yl)-3-methoxy-benzene [CAS4383-75-9] | ¹H NMR (600 MHz, CDCl₃) δ 11.41 (s, 1H), 9.04-9.06 (m, 1H), 8.66-8.68 (m, 1H), 8.25 (dd, J = 2.35, 7.34 Hz, 1H), 7.75 (d, J = 7.63 Hz, 1H), 7.53-7.56 (m, 1H), 7.22 (t, J = 7.78 Hz, 1H), 6.81 (d, J = 7.92 Hz, 1H), 6.74-6.77 (m, 2H), 3.79 (s, 3H), 2.69 (t, J = 7.63 Hz, 2H), 2.63 (t, J = 7.04 Hz, 2H), 1.85-1.91 (m, 2H), 1.76 (tdd, J = 7.04, 7.34, 7.48 Hz, 2H) |
| 4 | 5-(6-phenylhex-1-yn-1-yl)quinoline-8-carbaldehyde | 5-hexyn-1-yl-benzene [CAS100848-88-2] | ¹H NMR (600 MHz, CDCl₃) δ 11.41 (d, J = 0.59 Hz, 1H), 9.05 (dd, J = 1.76, 4.11 Hz, 1H), 8.67 (dd, J = 1.76, 8.51 Hz, 1H), 8.25 (d, J = 7.63 Hz, 1H), 7.75 (d, J = 7.34 Hz, 1H), 7.54 (dd, J = 4.26, 8.36 Hz, 1H), 7.28-7.31 (m, 2H), 7.19-7.23 (m, 3H), 2.72 (t, J = 7.63 Hz, 2H), 2.63 (t, J = 7.04 Hz, 2H), 1.85-1.91 (m, 2H), 1.74-1.79 (m, 2H) |
| 5 | 4-[6-(3-methoxyphenyl)hex-1-yn-1-yl]-1-naphthaldehyde | 1-(-5-hexyn-1-yl)-3-methoxy-benzene [CAS4383-75-9] | ¹H NMR (600 MHz, CDCl₃) δ 10.38 (s, 1H), 9.26 (d, J = 8.51 Hz, 1H), 8.42 (d, J = 7.63 Hz, 1H), 7.91 (d, J = 7.34 Hz, 1H), 7.74 (d, J = 7.34 Hz, 1H), 7.70 (ddd, J = 1.32, 6.97, 8.44 Hz, 1H), 7.64 (ddd, J = 1.17, 6.97, 8.29 Hz, 1H), 7.21 (t, J = 7.92 Hz, 1H), 6.82 (d, J = 7.92 Hz, 1H), 6.74-6.78 (m, 2H), 3.79 (s, 3H), 2.70 (t, J = 7.63 Hz, 2H), 2.64 (t, J = 7.04 Hz, 2H), 1.89 (qd, J = 7.48, 7.68 Hz, 2H), 1.78 (dt, J = 7.30, 15.26 Hz, 2H) |
| 6 | 4-(6-phenylhex-1-yn-1-yl)-1-naphthaldehyde | 5-hexyn-1-yl-benzene [CAS100848-88-2] | ¹H NMR (600 MHz, CDCl₃) δ 10.35 (s, 1H), 9.25 (d, J = 8.51 Hz, 1H), 8.42 (d, J = 8.22 Hz, 1H), 7.88 (d, J = 7.34 Hz, 1H), 7.72 (d, J = 7.34 Hz, 1H), 7.68-7.71 (m, 1H), 7.61-7.64 (m, 1H), 7.27-7.31 (m, 2H), 7.17-7.24 (m, 3H), 2.72 (t, J = 7.63 Hz, 2H), 2.63 (t, J = 7.04 Hz, 2H), 1.86-1.92 (m, 2H), 1.77 (tdd, J = 7.04, 7.34, 7.48 Hz, 2H) |

TABLE 1-continued

| Interm. No. | IUPAC name | Starting material | $^1$H NMR δ (ppm) for Compound |
|---|---|---|---|
| 7 | 5-(5-phenylpent-1-yn-1-yl)quinoline-8-carbaldehyde | 4-pentynyl-benzene [CAS1823-14-9] | $^1$H NMR (600 MHz, CDCl$_3$) δ 11.39 (d, J = 0.59 Hz, 1H), 8.99 (dd, J = 1.76, 4.11 Hz, 1H), 8.62 (dd, J = 2.64, 9.10 Hz, 1H), 8.20 (d, J = 7.04 Hz, 1H), 7.70 (d, J = 7.63 Hz, 1H), 7.49 (dd, J = 4.11, 8.51 Hz, 1H), 7.28-7.32 (m, 2H), 7.19-7.25 (m, 3H), 2.84 (t, J = 7.63 Hz, 2H), 2.59 (t, J = 7.04 Hz, 2H), 2.04 (qd, J = 7.19, 7.39 Hz, 2H) |

EXAMPLE 2

Intermediate 8

5-decylquinoline-8-carbaldehyde

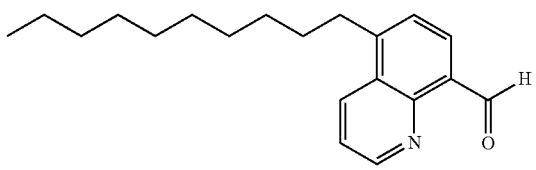 [SMILES: CCCCCCCCCCc1ccc(C=O)c2ncccc12]

A reaction mixture of Intermediate 1 (368 mg, 1.25 mmol) and 10% palladium on carbon in 30 mL ethyl acetate was submitted to H$_2$ balloon atmosphere with stirring at RT for 16 h. Filtration through a short column of SiO$_2$, concentration in vacuum, and purification by MPLC afforded 204 mg of Intermediate 8.

$^1$H NMR (300 MHz, CDCl$_3$) δ 11.42 (d, J=0.88 Hz, 1H), 9.04 (dd, J=1.76, 4.10 Hz, 1H), 8.44 (dd, J=1.76, 8.79 Hz, 1H), 8.26 (d, J=7.33 Hz, 1H), 7.53 (d, J=4.10 Hz, 1H), 7.40-7.68 (m, 1H), 3.11 (dd, J=7.90, 7.90 Hz, 2H), 1.62-1.90 (m, 2H), 1.13-1.55 (m, 14H), 0.88 (t, J=6.74 Hz, 3H).

Intermediates 9-15 were prepared from the corresponding aldehydes in a similar manner to the method described in Example 2 for Intermediate 3. The reactants used and the results are described below in Table 2.

TABLE 2

| Interm. No. | IUPAC name | Starting material | $^1$H NMR δ (ppm) for Compound |
|---|---|---|---|
| 9 | 5-(7-phenylheptyl)quinoline-8-carbaldehyde | Intermediate 2 | $^1$H NMR (300 MHz, CDCl$_3$) δ 11.42 (s, 1H), 9.03 (dd, J = 1.61, 4.25 Hz, 1H), 8.42 (dd, J = 1.76, 8.50 Hz, 1H), 8.25 (d, J = 7.33 Hz, 1H), 7.51 (t, J = 4.25 Hz, 1H), 7.49 (d, J = 1.17 Hz, 1H), 7.08-7.34 (m, 5H), 3.09 (dd, J = 7.90 Hz, 2H), 2.48-2.68 (m, 4H), 1.13-1.88 (m, 8H). |
| 10 | 5-(6-phenylhexyl)quinoline-8-carbaldehyde | Intermediate 4 | $^1$H NMR (600 MHz, CDCl$_3$) δ 11.43 (s, 1H), 8.97-9.04 (m, 1H), 8.37 (dd, J = 1.61, 8.66 Hz, 1H), 8.22 (d, J = 7.34 Hz, 1H), 7.41-7.51 (m, 2H), 7.24-7.30 (m, 2H), 7.13-7.21 (m, 3H), 3.05 (t, J = 7.48 Hz, 2H), 2.60 (t, J = 7.78 Hz, 2H), 1.71 (quin, J = 7.56 Hz, 2H), 1.63 (dt, J = 7.59, 15.04 Hz, 2H), 1.35-1.50 (m, 4H) |

TABLE 2-continued

| Interm. No. | IUPAC name | Starting material | $^1$H NMR δ (ppm) for Compound |
|---|---|---|---|
| 11 | 5-[6-(3-methoxyphenyl)hexyl]quinoline-8-carbaldehyde | Intermediate 3 | $^1$H NMR (300 MHz, CDCl$_3$) δ 11.42 (s, 1H), 9.04 (dd, J = 1.76, 4.10 Hz, 1H), 8.42 (dd, J = 1.76, 8.50 Hz, 1H), 8.25 (d, J = 7.62 Hz, 1H), 7.47-7.54 (m, 2H), 7.14-7.22 (m, 2H), 6.64-6.77 (m, 2H), 3.79 (s, 3H), 3.11 (d, J = 7.62 Hz, 1H), 3.02 (t, J = 7.90 Hz, 1H), 2.58 (t, J = 7.62 Hz, 2H), 1.36-1.80 (m, 8H) |
| 12 | 5-[6-(3-methoxyphenyl)hexyl]-1,2,3,4-tetrahydroquinoline-8-carbaldehyde | Intermediate 3 | $^1$H NMR (300 MHz, CDCl$_3$) δ 9.69 (s, 1H), 8.51 (br. s., 1H), 7.15-7.21 (m, 2H), 6.69-6.78 (m, 3H), 6.42 (d, J = 7.91 Hz, 1H), 3.78 (s, 3H), 3.39 (t, J = 4.54 Hz, 2H), 2.70 (t, J = 6.30 Hz, 2H), 2.58 (t, J = 7.00 Hz, 2H), 2.50 (t, J = 7.60 Hz, 2H), 1.92 (quin, J = 6.20 Hz, 2H), 1.48-1.67 (m, 4H), 1.34-1.44 (m, 4H) |
| 13 | 4-[6-(3-methoxyphenyl)hexyl]-1-naphthaldehyde | Intermediate 5 | $^1$H NMR (600 MHz, CDCl$_3$) δ 10.33 (s, 1H), 9.33 (dd, J = 0.88, 8.51 Hz, 1H), 8.11 (d, J = 8.51 Hz, 1H), 7.88 (d, J = 7.34 Hz, 1H), 7.67 (ddd, J = 1.32, 6.97, 8.44 Hz, 1H), 7.60 (ddd, J = 1.32, 6.97, 8.44 Hz, 1H), 7.46 (d, J = 7.34 Hz, 1H), 7.17-7.20 (m, 1H), 6.76 (d, J = 7.92 Hz, 1H), 6.71-6.73 (m, 2H), 3.78 (s, 3H), 3.12 (t, J = 7.30 Hz, 2H), 2.58 (t, J = 7.60 Hz, 2H), 1.77 (dt, J = 7.74, 15.33 Hz, 2H), 1.63 (dt, J = 7.59, 15.04 Hz, 2H), 1.38-1.50 (m, 4H) |
| 14 | 4-(6-phenylhexyl)-1-naphthaldehyde | Intermediate 6 | $^1$H NMR (300 MHz, CDCl$_3$) δ 10.34 (s, 1H), 9.33 (d, J = 8.51 Hz, 1H), 8.12 (d, J = 8.51 Hz, 1H), 7.90 (d, J = 7.04 Hz, 1H), 7.67-7.70 (m, 1H), 7.60-7.63 (m, 1H), 7.47 (d, J = 7.34 Hz, 1H), 7.26 (s, 1H), 7.27 (t, J = 7.00 Hz, 1H), 7.15-7.19 (m, 3H), 3.13 (t, J = 7.90 Hz, 2H), 2.61 (t, J = 7.78 Hz, 2H), 1.78 (ddd, J = 7.70, 7.92, 15.19 Hz, 2H), 1.64 (dt, J = 7.63, 15.26 Hz, 2H), 1.48 (ddd, J = 7.19, 7.41, 15.04 Hz, 2H), 1.41 (ddd, J = 7.00, 7.63, 14.97 Hz, 2H) |

TABLE 2-continued

| Interm. No. | IUPAC name | Starting material | $^1$H NMR δ (ppm) for Compound |
|---|---|---|---|
| 15 | 5-(5-phenylpentyl) quinoline-8-carbaldehyde | Intermediate 7 | $^1$H NMR (600 MHz, CDCl$_3$) δ 511.42 (d, J = 0.88 Hz, 1H), 9.03 (dd, J = 1.61, 3.96 Hz, 1H), 8.41 (dd, J = 1.61, 8.66 Hz, 1H), 8.24 (d, J = 7.34 Hz, 1H), 7.51 (dd, J = 4.25, 8.66 Hz, 1H), 7.48 (d, J = 7.63 Hz, 1H), 7.25-7.29 (m, 2H), 7.14-7.20 (m, 3H), 3.09 (t, J = 7.90 Hz, 2H), 2.61 (t, J = 7.78 Hz, 2H), 1.76 (ddd, J = 7.78, 7.92, 15.41 Hz, 2H), 1.69 (dt, J = 7.67, 15.48 Hz, 2H), 1.47 (quin, J = 7.63 Hz, 2H) |

EXAMPLE 3

Intermediate 16

4-[(1E)-dec-1-en-1-yl]-1-naphthaldehyde

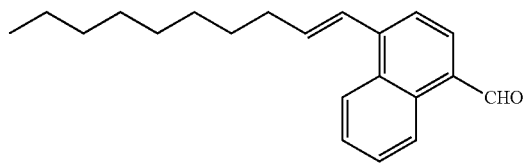 [SMILES: CCCCCCCC/C=C/c1ccc(C=O)c2ccccc12]

To a solution of 1-decyne (1378 g, 12.89 mmol) in THF (40 mL) at RT was added catecholborane (1M in THF, 21 mL, 21 mmol) with stirring. After heating to reflux for 3.5 h, the reaction mixture was cooled to RT, 4-bromonaphthalene-1-carboxaldehyde (CAS 50672-84-9) (2.0 g, 8.51 mmol) and tetrakis(triphenylphosphine)palladium(0) (893 mg, 0.77 mmol) were added. After the reaction mixture was stirred for 20 min at RT, Na$_2$CO$_3$ (2M solution, 12.9 mL) was added and heated to reflux for 16 h with stirring. The mixture was cooled to RT, quenched with water and extracted with ethyl acetate. The combined organic layers were washed with water, brine, and dried over magnesium sulfate. The resulting product was purified by MPLC (hexanes) to afford 353 mg of Intermediate 16 as yellow solid.

$^1$H NMR (600 MHz, CDCl$_3$) δ 10.31 (s, 1H), 9.29 (dd, J=0.59, 8.51 Hz, 1H), 8.17 (d, J=8.22 Hz, 1H), 7.86 (d, J=7.34 Hz, 1H), 7.63-7.67 (m, 2H), 7.57 (ddd, J=1.32, 6.97, 8.44 Hz, 1H), 7.11 (d, J=15.55 Hz, 1H), 6.36 (dt, J=7.04, 15.55 Hz, 1H), 2.34 (tdd, J=1.61, 7.04, 7.41 Hz, 2H), 1.55 (dt, J=7.30, 14.97 Hz, 2H), 1.24-1.42 (m, 10H), 0.89 (t, J=7.30 Hz, 3H)

EXAMPLE 4

Intermediate 17

1-(5-dec-1-yn-1-ylquinolin-8-yl)ethanone

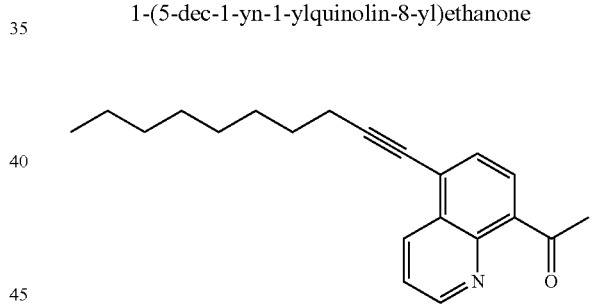

To a solution of Intermediate 1 (470 mg, 1.6 mmol) in THF (10 mL) at −78° C. was added methyl lithium (1.6 M in ether) dropwise with stirring. After 45 min, a solution of N-t-butyl benzenesulfinimidoyl chloride (518 mg, 2.4 mmol) in THF (3 mL) was added dropwise with stirring at −78° C. for 20 min. The reaction mixture was warmed to RT over 20 min then quenched with HCl (2M, 10 mL) and extracted with ethyl acetate. The organic layers were washed with 2M HCl and extracted with ethyl acetate, dried with magnesium sulfate, concentrated in vacuum and purified by MPLC (20% ethyl acetate in hexanes) to afford 123 mg of Intermediate 17.

$^1$H NMR (600 MHz, CDCl$_3$) δ 8.98 (dd, J=1.76, 3.81 Hz, 1H), 8.67 (dd, J=1.91, 8.36 Hz, 1H), 7.88 (d, J=7.63 Hz, 1H), 7.67 (d, J=7.63 Hz, 1H), 7.50 (dd, J=4.10, 8.51 Hz, 0H), 2.93

(s, 3H), 2.57 (t, J=7.19 Hz, 2H), 1.71 (dt, J=7.37, 14.89 Hz, 2H), 1.52 (ddd, J=7.19, 7.41, 15.04 Hz, 2H), 1.25-1.41 (m, 8H), 0.89 (t, J=6.90 Hz, 3H).

EXAMPLE 5

Compound 1

(3-{[(5-decylquinolin-8-yl)methyl]amino}propyl) phosphonic acid

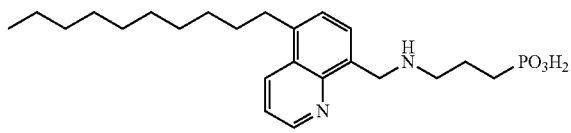

To a solution of Intermediate 8 (193 mg, 0.65 mmol) in MeOH (15 mL) was added (3-aminopropyl) phosphonic acid (90 mg) and tetrabutylammonium hydroxide (1M in MeOH). The reaction mixture was heated to 50° C. for 30 min with stirring, then sodium cyanoborohydride (41 mg, 0.65 mmol) was added. The reaction mixture was heated to 50° C. with stirring for 3 h. After cooling to RT, the mixture was dried over magnesium sulfate, concentrated and purified by MPLC (0-100% ethyl acetate in hexanes) to give 120 mg of Compound 1.

$^1$H NMR (600 MHz, CD$_3$OD) δ 8.98 (dd, J=1.61, 4.26 Hz, 1H), 8.60 (dd, J=1.61, 8.66 Hz, 1H), 7.79 (d, J=7.34 Hz, 1H), 7.63 (dd, J=4.25, 8.66 Hz, 1H), 7.48 (d, J=7.34 Hz, 1H), 4.69 (s, 2H), 3.17 (t, J=6.60 Hz, 2H), 3.12 (dd, J=7.90 Hz, 2H), 1.92-2.10 (m, J=7.01, 7.01, 17.09 Hz, 2H), 1.62-1.85 (m, 4H), 1.22-1.50 (m, 14H), 0.89 (t, J=7.30 Hz, 3H).

Compounds 2-24 were prepared from the corresponding aldehydes in a similar manner to the method described in Example 5 for Compound 1. The reactants used and the results are described below in Table 3.

TABLE 3

| Comp No. | IUPAC name | Structure | Starting material | $^1$H NMR δ (ppm) for Compound |
|---|---|---|---|---|
| 2 | (3-{[(5-dec-1-yn-1-ylquinolin-8-yl)methyl]amino}propyl) phosphonic acid | | Interm. 1 | $^1$H NMR (300 MHz, CD$_3$OD) δ 9.01 (dd, J = 1.61, 4.25 Hz, 1H), 8.72 (dd, J = 1.76, 8.50 Hz, 1H), 7.83 (d, J = 7.33 Hz, 1H), 7.67 (dd, J = 4.10, 9.10 Hz, 1H), 7.69 (d, J = 7.62 Hz, 1H), 4.72 (s, 2H), 3.19 (t, J = 6.74 Hz, 2H), 2.60 (t, J = 6.89 Hz, 2H), 1.91-2.18 (m, 2H), 1.61-1.81 (m, 4H), 1.48-1.61 (m, 2H), 1.23-1.48 (m, 8H), 0.89 (t, J = 7.00 Hz, 3H). |
| 3 | [3-({[5-(7-phenylhept-1-yn-1-yl)quinolin-8-yl]methyl}amino)propyl] phosphonic acid | | Interm. 2 | $^1$H NMR (600 MHz, CD$_3$OD) δ 8.97 (dd, J = 1.61, 4.26 Hz, 1H), 8.61 (dd, J = 1.76, 8.51 Hz, 1H), 7.81 (d, J = 7.63 Hz, 1H), 7.61 (d, J = 7.34 Hz, 1H), 7.59 (dd, J = 4.40, 8.51 Hz, 1H), 7.08-7.23 (m, 5H), 4.66 (s, 1H), 3.12 (t, J = 6.75 Hz, 2H), 2.62 (t, J = 7.48 Hz, 2H), 2.55 (t, J = 7.04 Hz, 2H), 2.02 (dqd, J = 6.46, 6.90, 16.73 Hz, 2H), 1.61-1.74 (m, 6H), 1.50-1.59 (m, 2H). |
| 4 | [3-({[5-(6-phenylhex-1-yn-1-yl)quinolin-8-yl]methyl}amino)propyl] phosphonic acid | | Interm. 4 | $^1$H NMR (600 MHz, CD$_3$OD) δ 8.99 (dd, J = 1.47, 4.11 Hz, 1H), 8.66 (dd, J = 1.47, 8.51 Hz, 1H), 7.82 (d, J = 7.63 Hz, 1H), 7.66 (d, J = 7.34 Hz, 1H), 7.62 (ddd, J = 1.47, 4.26, 8.36 Hz, 1H), 7.25 (s, 2H), 7.20 (d, J = 7.04 Hz, 2H), 7.15 (t, J = 7.63 Hz, 1H), 4.68 (s, 2H), 3.11-3.18 (m, 1H), 2.70 (t, J = 7.63 Hz, 2H), 2.61 (t, J = 7.04 Hz, 2H), 2.01 (dquin, J = 6.75, 17.00 Hz, 2H), 1.86 (dt, J = 7.63, 15.26 Hz, 2H), 1.62-1.76 (m, 4H) |

| Comp No. | IUPAC name | Starting material | ¹H NMR δ (ppm) for Compound |
|---|---|---|---|
| 5 | [3-({[5-(7-phenylheptyl)quinolin-8-yl]methyl}amino)propyl] phosphonic acid | Interm. 9 | ¹H NMR (600 MHz, CD₃OD) δ 8.96 (dd, J = 1.61, 4.26 Hz, 1H), 8.55 (dd, J = 1.47, 8.51 Hz, 1H), 7.78 (d, J = 7.34 Hz, 1H), 7.59 (dd, J = 4.11, 8.51 Hz, 1H), 7.44 (d, J = 7.34 Hz, 1H), 7.17-7.31 (m, 2H), 7.09-7.18 (m, 3H), 4.66 (s, 2H), 3.13 (t, J = 6.60 Hz, 2H), 3.08 (dd, J = 7.90, 8.51 Hz, 2H), 2.56 (t, J = 7.63 Hz, 2H), 2.01 (dquin, J = 6.75, 17.02 Hz, 2H), 1.62-1.79 (m, 4H), 1.58 (dt, J = 7.59, 15.04 Hz, 2H), 1.25-1.48 (m, 6H) |
| 6 | (3-{[(5-dec-1-yn-1-yl)quinolin-8-yl)methyl]amino}butyl) phosphonic acid | Interm. 17 | ¹H NMR (600 MHz, CD₃OD) δ 8.98 (dd, J = 1.76, 4.40 Hz, 1H), 8.75 (dd, J = 1.76, 8.22 Hz, 1H), 7.77 (d, J = 7.63 Hz, 1H), 7.70 (d, J = 7.34 Hz, 1H), 7.67 (dd, J = 4.25, 8.36 Hz, 1H), 5.04 (q, J = 6.70 Hz, 1H), 2.92 (ddd, J = 5.14, 7.41, 12.69 Hz, 1H), 2.80 (ddd, J = 5.30, 7.04, 12.00 Hz, 1H), 2.60 (t, J = 7.04 Hz, 2H), 1.92 (d, J = 6.75 Hz, 2H), 1.80 (d, J = 6.75 Hz, 3H), 1.71 (ddd, J = 7.19, 7.34, 14.82 Hz, 2H), 1.59-1.67 (m, J = 9.10, 15.00 Hz, 2H), 1.52-1.59 (m, 2H), 1.28-1.44 (m, 8H), 0.89 (t, J = 7.04 Hz, 3H) |
| 7 | [3-({[5-(6-phenylhexyl)quinolin-8-yl]methyl}amino)propyl] phosphonic acid | Interm. 10 | ¹H NMR (600 MHz, CD₃OD) δ 8.97 (dd, J = 1.47, 4.11 Hz, 1H), 8.57 (dd, J = 1.76, 8.51 Hz, 1H), 7.78 (d, J = 7.34 Hz, 1H), 7.61 (dd, J = 4.11, 8.51 Hz, 1H), 7.46 (d, J = 7.34 Hz, 1H), 7.16-7.26 (m, 1H), 7.13 (d, J = 7.63 Hz, 3H), 4.68 (s, 2H), 3.15 (t, J = 6.60 Hz, 2H), 3.10 (s, 2H), 2.58 (t, J = 7.63 Hz, 2H), 2.01 (dqd, J = 6.60, 6.87, 17.39 Hz, 2H), 1.56-1.76 (m, 6H), 1.35-1.50 (m, 4H) |
| 8 | [3-({[5-(5-phenylpent-1-yn-1-yl)quinolin-8-yl]methyl}amino)propyl] phosphonic acid | Interm. 7 | ¹H NMR (600 MHz, CD₃OD) δ: 8.99 (dd, J = 4.0, 1.6 Hz, 1H), 8.68 (dd, J = 8.1, 1.6 Hz, 1H), 7.83 (d, J = 7.3 Hz, 1H), 7.68 (d, J = 7.3 Hz, 1H), 7.64 (dd, J = 8.4, 4.3 Hz, 1H), 7.22-7.29 (m, 4H), 7.17 (t, J = 7.3 Hz, 1H), 4.69 (s, 2H), 3.15 (t, J = 6.7 Hz, 2H), 2.83 (t, J = 7.5 Hz, 2H), 2.57 (t, J = 7.0 Hz, 2H), 1.96-2.07 (m, 4H), 1.63-1.71 (m, 2H) |

TABLE 3-continued

| Comp No. | IUPAC name | Starting material | $^1$H NMR δ (ppm) for Compound |
|---|---|---|---|
| 9 | [3-({[5-(5-phenylpentyl)quinolin-8-yl]methyl}amino)propyl] phosphonic acid | Interm. 15 | $^1$H NMR (600 MHz, CD$_3$OD) δ: 8.96 (dd, J = 4.1, 1.5 Hz, 1H), 8.53 (dd, J = 8.7, 1.6 Hz, 1H), 7.77 (d, J = 7.0 Hz, 1H), 7.59 (dd, J = 8.5, 4.1 Hz, 1H), 7.41 (d, J = 7.3 Hz, 1H), 7.20-7.23 (m, 2H), 7.10-7.13 (m, 3H), 4.65 (s, 2H), 3.12 (t, J = 6.7 Hz, 2H), 3.06 (t, J = 7.6 Hz, 2H), 2.57 (t, J = 7.6 Hz, 2H), 2.02 (dquin, J = 17.0, 7.0 Hz, 2H), 1.62-1.73 (m, 6H), 1.40-1.45 (m, 2H) |
| 10 | 2-({[5-(6-phenylhexyl)quinolin-8-yl]methyl}amino)ethanol | Interm. 10 | $^1$H NMR (600 MHz, CDCl$_3$) δ 8.89 (dd, J = 1.76, 4.11 Hz, 1H), 8.23-8.48 (m, 1H), 7.56 (d, J = 7.34 Hz, 1H), 7.43 (dd, J = 4.11, 8.51 Hz, 1H), 7.25-7.31 (m, 3H), 7.15-7.19 (m, 3H), 4.32 (s, 2H), 3.75 (t, J = 5.00 Hz, 2H), 3.00-3.03 (m, J = 7.92 Hz, 2H), 2.86 (t, J = 5.30 Hz, 2H), 2.60 (t, J = 7.63 Hz, 2H), 1.70 (dt, J = 7.52, 15.19 Hz, 2H), 1.63 (dt, J = 7.52, 15.19 Hz, 2H), 1.36-1.47 (m, 4H) |
| 11 | 2-({[5-(6-phenylhexyl)quinolin-8-yl]methyl}amino)ethyl dihydrogen phosphate | Interm. 10 | $^1$H NMR (600 MHz, CD$_3$OD) δ: 9.02-9.03 (m, 1H), 8.68-8.71 (m, 1H), 7.82 (dd, J = 7.2, 2.5 Hz, 1H), 7.70 (ddd, J = 8.7, 4.4, 1.3 Hz, 1H), 7.52 (d, J = 7.3 Hz, 1H), 7.21-7.24 (m, 2H), 7.13 (d, J = 7.6 Hz, 3H), 4.80 (s, 2H), 4.29-4.33 (m, 2H), 3.43 (t, J = 4.5 Hz, 2H), 3.14 (t, J = 7.6 Hz, 2H), 2.59 (t, J = 7.5 Hz, 2H), 1.73 (dt, J = 15.0, 7.6 Hz, 2H), 1.61 (dt, J = 15.0, 7.5 Hz, 2H), 1.36-1.49 (m, 4H) |
| 12 | {3-[({5-[6-(3-methoxyphenyl)hex-1-yn-1-yl]quinolin-8-yl}methyl)amino]propyl} phosphonic acid | Interm. 3 | $^1$H NMR (600 MHz, CD$_3$OD) δ 9.02 (dd, J = 1.76, 4.40 Hz, 1H), 8.72 (dd, J = 1.61, 8.36 Hz, 1H), 7.81 (d, J = 7.34 Hz, 1H), 7.71 (d, J = 7.63 Hz, 1H), 7.68 (dd, J = 4.11, 8.51 Hz, 1H), 7.17 (t, J = 7.78 Hz, 1H), 6.77-6.80 (m, 2H), 6.73 (dd, J = 3.08, 7.78 Hz, 1H), 4.75 (s, 2H), 3.75 (s, 3H), 3.24 (t, J = 7.30 Hz, 2H), 2.69 (t, J = 7.63 Hz, 2H), 2.64 (t, J = 6.90 Hz, 2H), 2.08 (tdd, J = 7.63, 7.78, 14.89 Hz, 2H), 1.81-1.90 (m, 4H), 1.71-1.76 (m, 2H) |

TABLE 3-continued

| Comp No. | IUPAC name | Starting material | $^1$H NMR δ (ppm) for Compound |
|---|---|---|---|
| 13 | {3-[({5-[6-(3-methoxyphenyl)hexyl]quinolin-8-yl}methyl)amino]propyl} phosphonic acid | Interm. 11 | $^1$H NMR (600 MHz, CD$_3$OD) δ 8.97 (dd, J = 1.47, 4.11 Hz, 1H), 8.58 (dd, J = 1.61, 8.66 Hz, 1H), 7.78 (d, J = 7.34 Hz, 1H), 7.62 (dd, J = 4.11, 8.51 Hz, 1H), 7.46 (d, J = 7.04 Hz, 1H), 7.12-7.15 (m, 1H), 6.69-6.72 (m, 3H), 4.69 (s, 2H), 3.75 (s, 3H), 3.16 (t, J = 6.60 Hz, 2H), 3.11 (t, J = 7.63 Hz, 2H), 2.55 (t, J = 7.78 Hz, 2H), 2.01 (ddt, J = 6.86, 13.68, 17.20 Hz, 2H), 1.66-1.74 (m, 4H), 1.60 (dt, J = 7.52, 15.19 Hz, 2H), 1.45 (ddd, J = 7.34, 7.48, 15.11 Hz, 2H), 1.35-1.41 (m, 2H) |
| 14 | {3-[({5-[6-(3-methoxyphenyl)hexyl]-5,6,7,8-tetrahydroquinolin-8-yl}methyl)amino]propyl} phosphonic acid | Interm. 12 | $^1$H NMR (600 MHz, CD$_3$OD) δ 7.30 (d, J = 7.92 Hz, 1H), 7.15 (dd, J = 7.63, 8.80 Hz, 1H), 7.10 (d, J = 7.63 Hz, 1H), 6.70-6.74 (m, 4H), 4.23 (s, 2H), 3.76 (s, 3H), 3.48-101 3.50 (m, 2H), 3.24 (t, J = 7.34 Hz, 2H), 2.85 (t, J = 6.46 Hz, 2H), 2.62 (t, J = 7.60 Hz, 2H), 2.57 (t, J = 7.63 Hz, 2H), 2.01-2.11 (m, 4H), 1.85 (dt, J = 7.34, 18.49 Hz, 2H), 1.54-1.64 (m, 4H), 1.35-1.44 (m, 4H) |
| 15 | {3-[({4-[(1E)-dec-1-en-1-yl]-1-naphthyl}methyl)amino]prop-yl}phosphonic acid | Interm. 16 | $^1$H NMR (600 MHz, CD$_3$OD) δ 8.26 (d, J = 7.92 Hz, 1H), 8.14 (d, J = 8.22 Hz, 1H), 7.68 (ddd, J = 1.17, 6.75, 8.51 Hz, 1H), 7.61-7.64 (m, 3H), 7.18 (d, J = 15.55 Hz, 1H), 6.33 (dt, J = 7.04, 15.55 Hz, 1H), 4.70 (s, 2H), 3.29 (t, J = 7.60 Hz, 2H), 2.37 (tdd, J = 1.47, 7.04, 7.60 Hz, 2H), 2.07 (tt, J = 7.63, 15.26 Hz, 2H), 1.85 (dt, J = 7.63, 18.49 Hz, 2H), 1.58 (quin, J = 7.41 Hz, 2H), 1.30-1.47 (m, 5H), 0.90 (t, J = 7.30 Hz, 3H) |
| 16 | [3-({[4-(6-phenylhex-1-yn-1-yl)-1-naphthyl]methyl}amino)prop-yl]phosphonic acid | Interm. 6 | $^1$H NMR (600 MHz, CD$_3$OD) δ 8.43 (dd, J = 0.59, 8.22 Hz, 1H), 8.16 (d, J = 8.51 Hz, 1H), 7.71 (ddd, J = 1.47, 6.97, 8.29 Hz, 1H), 7.64-7.67 (m, 1H), 7.63 (dd, J = 7.34, 23.48 Hz, 2H), 7.21-7.27 (m, 4H), 7.14-7.17 (m, 1H), 4.71 (s, 2H), 3.30 (t, J = 7.90 Hz, 2H), 2.72 (t, J = 7.63 Hz, 2H), 2.63 (t, J = 7.04 Hz, 2H), 2.07 (tt, J = 7.63, 15.26 Hz, 2H), 1.82-1.92 (m, 4H), 1.74 (ddd, J = 7.04, 7.90, 15.26 Hz, 2H) |

TABLE 3-continued

| Comp No. | IUPAC name | Starting material | $^1$H NMR δ (ppm) for Compound |
|---|---|---|---|
| 17 | 2-({[4-(6-phenylhexyl)-1-naphthyl]methyl}amino)ethanol | Interm. 14 | $^1$H NMR (600 MHz, CD$_3$OD) δ8.02-8.11 (m, 2H), 7.46-7.53 (m, 2H), 7.34-7.39 (m, 1H), 7.18-7.25 (m, 3H), 7.08-7.12 (m, 3H), 4.15-4.19 (m, 2H), 3.68 (q, J = 5.67 Hz, 2H), 2.96-3.04 (m, 2H), 2.79-2.84 (m, 2H), 2.49-2.56 (m, 2H), 1.63-1.71 (m, 2H), 1.52-1.60 (m, 2H), 1.29-1.44 (m, 4H) |
| 18 | 2-({[4-(6-phenylhexyl)-1-naphthyl]methyl}amino)ethyl dihydrogen phosphate | Interm. 14 | $^1$H NMR (600 MHz, CD$_3$OD) δ 8.16-8.21 (m, 2H), 7.60-7.71 (m, 3H), 7.41 (d, J = 7.33 Hz, 1H), 7.19-7.27 (m, 2H), 7.10-7.16 (m, 3H), 4.76 (s, 2H), 4.30-4.36 (m, 2H), 3.48 (t, J = 4.84 Hz, 2H), 3.12 (t, J = 7.90 Hz, 2H), 2.59 (t, J = 7.90 Hz, 2H), 1.75 (quin, J = 7.55 Hz, 2H), 1.62 (dt, J = 7.44, 14.72 Hz, 2H), 1.36-1.52 (m, 4H) |
| 19 | [3-({[4-(6-phenylhexyl)-1-naphthyl]methyl}amino)propyl]phosphonic acid | Interm. 14 | $^1$H NMR (600 MHz, CD$_3$OD) δ 8.14 (d, J = 8.51 Hz, 2H), 7.60-7.66 (m, 2H), 7.58 (d, J = 7.34 Hz, 1H), 7.38 (d, J = 7.34 Hz, 1H), 7.21-7.24 (m, 2H), 7.11-7.14 (m, 3H), 4.60 (s, 2H), 3.20 (t, J = 6.31 Hz, 2H), 3.09 (t, J = 7.30 Hz, 2H), 2.59 (t, J = 7.00 Hz, 2H), 2.01 (ddt, J = 6.60, 12.95, 19.33 Hz, 2H), 1.69-1.76 (m, 4H), 1.61 (dt, J = 7.63, 15.26 Hz, 2H), 1.46 (dt, J = 7.30, 15.26 Hz, 2H), 1.37-1.42 (m, 2H) |
| 20 | {3-[({4-[6-(3-methoxyphenyl)hex-1-yn-1-yl]-1-naphthyl}methyl)amino]propyl}phosphonic acid | Interm. 5 | $^1$H NMR (600 MHz, CD$_3$OD) δ 8.43 (dd, J = 0.73, 8.36 Hz, 1H), 8.16 (d, J = 8.51 Hz, 1H), 7.71 (ddd, J = 1.50, 7.00, 8.51 Hz, 1H), 7.64-7.67 (m, 1H), 7.65 (d, J = 7.34 Hz, 1H), 7.61 (d, J = 7.34 Hz, 1H), 7.17 (t, J = 7.78 Hz, 1H), 6.78-6.81 (m, 2H), 6.73 (dd, J = 2.35, 8.22 Hz, 1H), 4.71 (s, 2H), 3.75 (s, 3H), 3.30 (t, J = 7.90 Hz, 2H), 2.69 (t, J = 7.63 Hz, 2H), 2.63 (t, J = 6.90 Hz, 2H), 2.07 (tt, J = 7.63, 15.26 Hz, 2H), 1.82-1.92 (m, 4H), 1.74 (dt, J = 7.34, 15.26 Hz, 2H) |

TABLE 3-continued

| Comp No. | IUPAC name | Starting material | $^1$H NMR δ (ppm) for Compound |
|---|---|---|---|
| 21 | 2-[({4-[6-(3-methoxyphenyl)hex-1-yn-1-yl]-1-naphthyl}methyl)amino]ethyl dihydrogen phosphate | Interm. 5 | $^1$H NMR (600 MHz, CD$_3$OD) δ 8.43 (d, J = 8.22 Hz, 1H), 8.18 (d, J = 8.51 Hz, 1H), 7.72 (ddd, J = 1.32, 6.97, 8.44 Hz, 1H), 7.66 (d, J = 7.04 Hz, 1H), 7.65-7.68 (m, 1H), 7.63 (d, J = 7.34 Hz, 1H), 7.17 (t, J = 7.92 Hz, 1H), 6.78-6.81 (m, 2H), 6.73 (dd, J = 2.49, 8.07 Hz, 1H), 4.78 (s, 2H), 4.31-4.34 (m, 2H), 3.74 (s, 3H), 3.49 (dd, J = 4.69, 5.28 Hz, 2H), 2.69 (t, J = 7.63 Hz, 2H), 2.63 (t, J = 7.04 Hz, 2H), 1.87-1.92 (m, 2H), 1.74 (tdd, J = 7.04, 7.26, 7.37 Hz, 2H) |
| 22 | {3-[({4-[6-(3-methoxyphenyl)hexyl]-1-naphthyl}methyl)amino]propyl}phosphonic acid | Interm. 13 | $^1$H NMR (600 MHz, CD$_3$OD) δ 8.16-8.21 (m, 2H), 7.60-7.70 (m, 3H), 7.43 (d, J = 7.34 Hz, 1H), 7.16 (t, J = 7.60 Hz, 1H), 6.71-6.76 (m, 3H), 4.72 (s, 2H), 3.78 (s, 3H), 3.30-3.33 (m, 2H), 3.13 (t, J = 7.30 Hz, 2H), 2.58 (t, J = 7.90 Hz, 2H), 2.07-2.15 (m, 2H), 1.84-1.91 (m, 2H), 1.68-1.79 (m, 3H), 1.60-1.65 (m, 1H), 1.39-1.51 (m, 4H) |
| 23 | 2-[({4-[6-(3-methoxyphenyl)hexyl]-1-naphthyl}methyl)amino]ethanol | Interm. 13 | $^1$H NMR (600 MHz, CD$_3$OD) δ 8.09 (dd, J = 1.32, 8.07 Hz, 1H), 8.05 (dd, J = 1.32, 8.07 Hz, 1H), 7.50 (tdd, J = 6.02, 7.48, 7.78 Hz, 2H), 7.36 (d, J = 7.34 Hz, 1H), 7.23 (d, J = 7.34 Hz, 1H), 7.12 (dd, J = 7.19, 8.95 Hz, 1H), 6.67-6.70 (m, 3H), 4.17 (s, 2H), 3.72 (s, 3H), 3.68 (t, J = 5.60 Hz, 2H), 3.00 (t, J = 7.90 Hz, 2H), 2.81 (t, J = 5.90 Hz, 2H), 2.51 (t, J = 7.90 Hz, 2H), 1.67 (dt, J = 7.52, 15.19 Hz, 2H), 1.56 (dt, J = 7.59, 15.04 Hz, 2H), 1.31-1.43 (m, 4H) |

TABLE 3-continued

| Comp No. | IUPAC name | Starting material | $^1$H NMR δ (ppm) for Compound |
|---|---|---|---|
| 24 | 2-[({4-[6-(3-methoxyphenyl)hexyl]-1-naphthyl}methyl)amino]ethyl dihydrogen phosphate | Interm. 13 | $^1$H NMR (600 MHz, CD$_3$OD) δ 8.18 (t, J = 8.95 Hz, 2H), 7.67 (ddd, J = 1.17, 6.75, 8.22 Hz, 1H), 7.63 (ddd, J = 1.47, 6.75, 8.51 Hz, 1H), 7.60 (d, J = 7.04 Hz, 1H), 7.41 (d, J = 7.34 Hz, 1H), 7.13-7.16 (m, 1H), 6.70-6.73 (m, 3H), 4.76 (s, 2H), 4.31-4.34 (m, 2H), 3.75 (s, 3H), 3.47 (t, J = 4.70 Hz, 2H), 3.12 (t, J = 7.60 Hz, 2H), 2.56 (t, J = 7.30 Hz, 2H), 1.74 (dt, J = 7.63, 15.26 Hz, 2H), 1.61 (dt, J = 7.59, 15.04 Hz, 2H), 1.37-1.49 (m, 4H) |

EXAMPLE 6

Biological Data

Novel compounds were synthesized and tested for S1P1 activity using the GTP γ$^{35}$S binding assay. These compounds may be assessed for their ability to activate or block activation of the human S1P1 receptor in cells stably expressing the S1P1 receptor. GTP γ$^{35}$S binding was measured in the medium containing (mM) HEPES 25, pH 7.4, MgCl$_2$ 10, NaCl 100, dithitothreitol 0.5, digitonin 0.003%, 0.2 nM GTP γ$^{35}$S, and 5 μg membrane protein in a volume of 150 μl. Test compounds were included in the concentration range from 0.08 to 5,000 nM unless indicated otherwise. Membranes were incubated with 100 μM 5'-adenylylimmidodiphosphate for 30 min, and subsequently with 10 μM GDP for 10 min on ice. Drug solutions and membrane were mixed, and then reactions were initiated by adding GTP γ$^{35}$S and continued for 30 min at 25° C. Reaction mixtures were filtered over Whatman GF/B filters under vacuum, and washed three times with 3 mL of ice-cold buffer (HEPES 25, pH7.4, MgCl$_2$ 10 and NaCl 100). Filters were dried and mixed with scintillant, and counted for $^{35}$S activity using a β-counter. Agonist-induced GTP γ$^{35}$S binding was obtained by subtracting that in the absence of agonist. Binding data were analyzed using a non-linear regression method. In case of antagonist assay, the reaction mixture contained 10 nM S1P1 in the presence of test antagonist at concentrations ranging from 0.08 to 5000 nM. Activity potency: S1P1 receptor from GTP γ$^{35}$S: nM, (EC$_{50}$).

TABLE 4

| IUPAC name | S1P1 EC$_{50}$ (nM) |
|---|---|
| (3-{[(5-decylquinolin-8-yl)methyl]amino}propyl)phosphonic acid | 1.53 |
| (3-{[(5-dec-1-yn-1-ylquinolin-8-yl)methyl] amino}propyl)phosphonic acid | 3.39 |
| (3-{[(5-dec-1-yn-1-ylquinolin-8-yl)methyl]amino}butyl)phosphonic acid | 126 |
| [3-({[5-(7-phenylhept-1-yn-1-yl)quinolin-8-yl]methyl}amino)propyl]phosphonic acid | 94 |
| [3-({[5-(7-phenylheptyl)quinolin-8-yl]methyl}amino)propyl]phosphonic acid | 173 |
| [3-({[5-(6-phenylhex-1-yn-1-yl)quinolin-8-yl]methyl}amino)propyl]phosphonic acid | 204 |
| [3-({[5-(6-phenylhexyl)quinolin-8-yl]methyl}amino)propyl]phosphonic acid | 5.45 |
| [3-({[5-(5-phenylpent-1-yn-1-yl)quinolin-8-yl]methyl}amino)propyl]phosphonic acid | 543 |
| 2-({[5-(6-phenylhexyl)quinolin-8-yl]methyl}amino)ethanol | 637 |
| 2-({[5-(6-phenylhexyl)quinolin-8-yl]methyl}amino)ethyl dihydrogen phosphate | 2.19 |
| {3-[({4-[(1E)-dec-1-en-1-yl]-1-naphthyl}methyl)amino]propyl}phosphonic acid | 138 |
| {3-[({5-[6-(3-methoxyphenyl)hexyl]quinolin-8-yl}methyl)amino]propyl}phosphonic acid | 7.68 |
| {3-[({5-[6-(3-methoxyphenyl)hex-1-yn-1-yl]quinolin-8-yl}methyl)amino]propyl}phosphonic acid | 18.3 |
| [3-({[4-(6-phenylhex-1-yn-1-yl)-1-naphthyl]methyl}amino)propyl]phosphonic acid | 4.88 |
| [3-({[4-(6-phenylhexyl)-1-naphthyl]methyl}amino)propyl]phosphonic acid | 5.59 |
| 2-({[4-(6-phenylhexyl)-1-naphthyl]methyl}amino)ethyl dihydrogen phosphate | 55.5 |

EXAMPLE 7

Lymphopenia Assay in Mice

Test drugs are prepared in a solution containing 3% (w/v) 2-hydroxy propyl β-cyclodextrin (HPBCD) and 1% DMSO to a final concentration of 1 mg/ml, and subcutaneously injected to female C57BL6 mice (CHARLES RIVERS) weighing 20-25 g at the dose of 10 mg/Kg. Blood samples are obtained by puncturing the submandibular skin with a Goldenrod animal lancet at 5, 24, 48, 72, and 96 hrs post drug application. Blood is collected into microvettes (SARSTEDT) containing EDTA tripotassium salt. Lymphocytes in blood samples are counted using a HEMAVET Multispecies Hematology System, HEMAVET HV950FS (Drew Scientific Inc.). (Hale, J. et al Bioorg. & Med. Chem. Lett. 14 (2004) 3351).

A lymphopenia assay in mice, as previously described, was employed to measure the in vivo blood lymphocyte depletion after dosing Compound 5 (FIG. 1). These S1P agonists (or modulators) are useful for S1P-related diseases, and exemplified by the lymphopenia in vivo response. In general, test compounds were prepared in a solution containing 3% (w/v) 2-hydroxy propyl β-cyclodextrin (HPBCD) and 1% DMSO to a final concentration of 1 mg/ml, and subcutaneously injected to female C57BL6 mice (CHARLES RIVERS) weighing 20-25 g at the dose of 10 mg/Kg or 2 mg/Kg. Blood samples were obtained by puncturing the submandibular skin with a Goldenrod animal lancet at 24, 48, 72 and 96 hrs post drug application. Blood was collected into microvettes (SARSTEDT) containing EDTA tripotassium salt. Lymphocytes in blood samples were counted using a HEMAVET Multispecies Hematology System, HEMAVET HV950FS (Drew Scientific Inc.). Results are shown in FIG. 1 that depict lowered lymphocyte count after 24 hours (<1 number of lymphocytes $10^3/\mu L$ blood).

What is claimed is:

1. A method of treating an immunosuppressant disorder associated with the sphingosine-1-phosphate receptor modulation, wherein the immunosuppressant disorder is selected from: rheumatoid arthritis, psoriasis, atherosclerosis, autoimmune uveitis, dry eye, inflammatory bowel diseases, atopic allergy, atopic dermatitis, contact dermatitis, multiple sclerosis, Sjogren's syndrome and organ transplant rejection, in a mammal in need thereof, which comprises administering to a mammal in need thereof, a pharmaceutical composition comprising a therapeutically effective amount of at least one compound represented by Formula I or a pharmaceutically acceptable salt thereof:

Formula I wherein:

represents a single bond

—CH$_2$—CH$_2$— or a double bond

—CH=CH— represents a single bond

—CH$_2$—CH$_2$— or a double bond

—CH=CH—;

or a triple bond

—C≡C—;

A is substituted or unsubstituted $C_{6-10}$ aryl, substituted or unsubstituted heterocycle substituted or unsubstituted $C_{5-8}$ cycloalkyl, substituted or unsubstituted $C_{5-8}$ cycloalkenyl, or H;
$R^2$ is H, halogen, —$OC_{1-3}$ alkyl, substituted or unsubstituted $C_{1-3}$ alkyl, CN, $C(O)R^8$, $NR^9R^{10}$ or hydroxyl;
$R^3$ is H, halogen, substituted or unsubstituted $C_{1-3}$ alkyl, $C(O)R^8$ or hydroxyl;
$R^4$ is $OPO_3H_2$, carboxylic acid, $PO_3H_2$, $C_{1-6}$ alkyl, —$S(O)_2H$, —$P(O)MeOH$, —$P(O)(H)OH$ or $OR^{11}$;
$R^5$ is H, halogen, —$OC_{1-3}$ alkyl, substituted or unsubstituted $C_{1-3}$ alkyl, CN, $C(O)R^8$, $NR^9R^{10}$ or hydroxyl;
$R^6$ is H, halogen, —$OC_{1-3}$ alkyl, substituted or unsubstituted $C_{1-3}$ alkyl, CN, $C(O)R^8$, $NR^9R^{10}$ or hydroxyl;
$R^7$ is H, halogen, —$OC_{1-3}$ alkyl, substituted or unsubstituted $C_{1-3}$ alkyl, CN, $C(O)R^8$, $NR^9R^{10}$ or hydroxyl;
$R^8$ is H, $OR^{11}$ or substituted or unsubstituted $C_{1-3}$ alkyl;
$R^9$ is H or substituted or unsubstituted $C_{1-3}$ alkyl;
$R^{10}$ is H or substituted or unsubstituted $C_{1-3}$ alkyl;
$R^{11}$ is H or substituted or unsubstituted $C_{1-3}$ alkyl;
$L^1$ is O, S, NH or $CH_2$;
$L^2$ is O, S, NH or $CH_2$;
a is 0 or 1;
b is 0, 1, 2 or 3;
c is 1, 2, 3 or 4;
d is 1, 2 or 3; with the provisos
when a is 1 then

—$R^1$=— represents

—N=CH—; or —CH=CH—; or

—$CH_2$—$CH_2$—; or —O—$CH_2$—; or

-continued

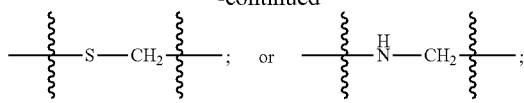

and
when a is 0 then $R^1$ is O, S, NH, or $CH_2$.

2. The method according to claim 1, wherein:

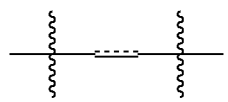

represents a double bond

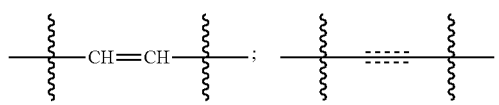

represents a single bond

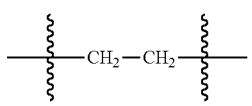

or a triple bond

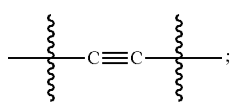 [SMILES: *C#C*]

A is substituted or unsubstituted $C_{6-10}$ aryl or H;
$R^2$ is H or substituted or unsubstituted $C_{1-3}$ alkyl;
$R^3$ is H;
$R^4$ is $PO_3H_2$, $OPO_3H_2$ or $OR^{11}$;
$R^5$ is H;
$R^6$ is H;
$R^7$ is H;
$R^{11}$ is H or substituted or unsubstituted $C_{1-3}$ alkyl;
$L^1$ is $CH_2$;
$L^2$ is $CH_2$;
a is 1;
b is 1;
c is 1, 2, 3 or 4;
d is 1, 2 or 3; and

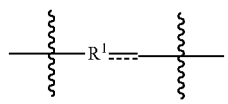

represents

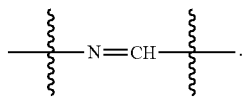

3. The method according to claim 1, wherein:

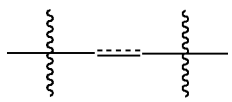

represents a double bond

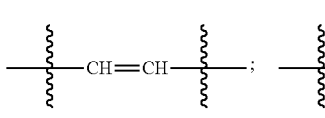

represents a triple bond

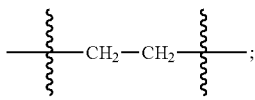

A is substituted or unsubstituted phenyl or H;
$R^2$ is H;
$R^3$ is H;
$R^4$ is $OPO_3H_2$, $OPO_3H_2$, or $OR^{11}$;
$R^5$ is H;
$R^6$ is H;
$R^7$ is H;
$R^{11}$ is H;
$L^1$ is $CH_2$;
$L^2$ is $CH_2$;
a is 1;
b is 1;
c is 1, 2, 3 or 4;
d is 1, 2 or 3; and

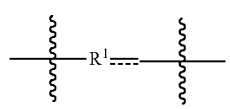

represents

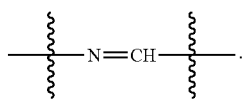

4. The method according to claim 1, wherein:

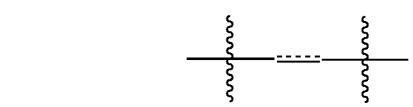

represents a double bond

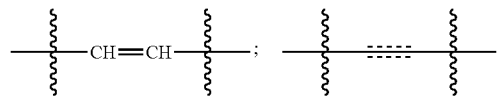

represents a triple bond

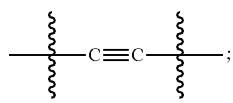 [SMILES: *C#C*]

A is substituted or unsubstituted phenyl or H;
$R^2$ is H or substituted or unsubstituted $C_{1-3}$ alkyl;
$R^3$ is H;
$R^4$ is $OPO_3H_2$;
$R^5$ is H;
$R^6$ is H;
$R^7$ is H;
$L^1$ is $CH_2$;
$L^2$ is $CH_2$;
a is 1;
b is 1;
c is 1, 2 or 4;
d is 1, 2 or 3; and

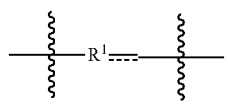

represents

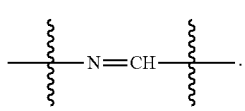 [SMILES: *C=N*]

5. The method according to claim 1, wherein:

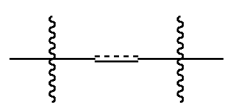

represents a double bond

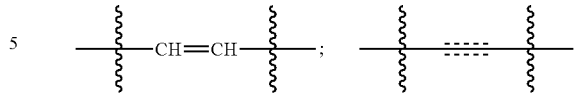

represents a triple bond

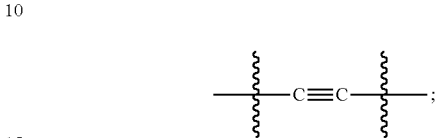

A is substituted or unsubstituted phenyl;
$R^2$ is H or substituted or unsubstituted $C_{1-3}$ alkyl;
$R^3$ is H;
$R^4$ is $OPO_3H_2$;
$R^5$ is H;
$R^6$ is H;
$R^7$ is H;
$L^1$ is $CH_2$;
$L^2$ is $CH_2$;
a is 1;
b is 1;
c is 1 or 2;
d is 1, 2 or 3; and

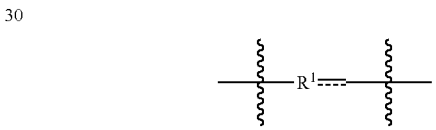

represents

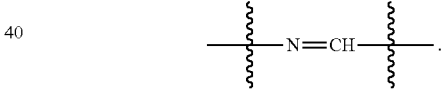

6. The method according to claim 1, wherein:

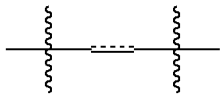

represents a double bond

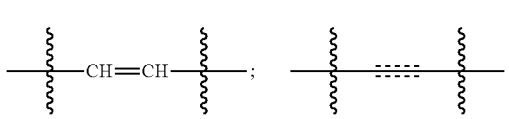

represents a triple bond

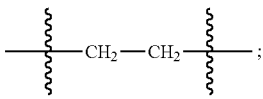

A is substituted or unsubstituted phenyl;
$R^2$ is H;
$R^3$ is H;
$R^4$ is $OPO_3H_2$, $OPO_3H_2$, or $OR^{11}$;
$R^5$ is H;
$R^6$ is H;
$R^7$ is H;
$R^{11}$ is H;
$L^1$ is $CH_2$;
$L^2$ is $CH_2$;
a is 1;
b is 1;
c is 2 or 3;
d is 2 or 3; and

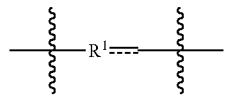

represents

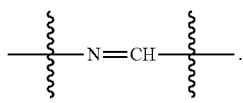

7. The method according to claim 1, wherein:

represents a single bond

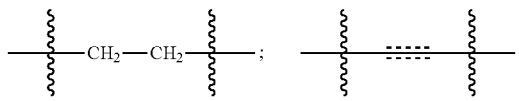

represents a triple bond

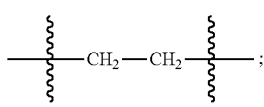 [SMILES: *CC*]

A is substituted phenyl;
$R^2$ is H;
$R^3$ is H;
$R^4$ is, $PO_3H_2$;
$R^5$ is H;
$R^6$ is H;
$R^7$ is H;
$L^1$ is $CH_2$;
$L^2$ is $CH_2$;
a is 1;
b is 1;
c is 2;
d is 1; and

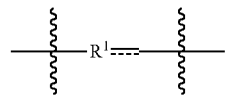

represents

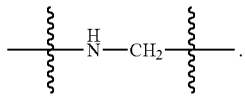 [SMILES: *CN*]

8. The method according to claim 1, wherein the compound is selected from:
- (3-{[(5-decylquinolin-8-yl)methyl]amino}propyl)phosphonic acid;
- (3-{[(5-dec-1-yn-1-ylquinolin-8-yl)methyl]amino}propyl)phosphonic acid;
- [3-({[5-(7-phenylhept-1-yn-1-yl)quinolin-8-yl]methyl}amino)propyl]phosphonic acid;
- [3-({[5-(6-phenylhex-1-yn-1-yl)quinolin-8-yl]methyl}amino)propyl]phosphonic acid;
- [3-({[5-(7-phenylheptyl)quinolin-8-yl]methyl}amino)propyl]phosphonic acid;
- (3-{[(5-dec-1-yn-1-ylquinolin-8-yl)methyl]amino}butyl)phosphonic acid;
- [3-({[5-(6-phenylhexyl)quinolin-8-yl]methyl}amino)propyl]phosphonic acid;
- [3-({[5-(5-phenylpent-1-yn-1-yl)quinolin-8-yl]methyl}amino)propyl]phosphonic acid;
- [3-({[5-(5-phenylpentyl)quinolin-8-yl]methyl}amino)propyl]phosphonic acid;
- 2-({[5-(6-phenylhexyl)quinolin-8-yl]methyl}amino)ethanol;
- 2-({[5-(6-phenylhexyl)quinolin-8-yl]methyl}amino)ethyl dihydrogen phosphate;
- {3-[({5-[6-(3-methoxyphenyl)hex-1-yn-1-yl]quinolin-8-yl}methyl)amino]propyl}phosphonic acid;
- {3-[({5-[6-(3-methoxyphenyl)hexyl]quinolin-8-yl}methyl)amino]propyl}phosphonic acid;
- {3-[({5-[6-(3-methoxyphenyl)hexyl]-5,6,7,8-tetrahydroquinolin-8-yl}methyl)amino]propyl}phosphonic acid;
- {3-[({4-[(1E)dec-1-en-1-yl]-1-naphthyl}methyl)amino]propyl}phosphonic acid;
- [3-({[4-(6-phenylhex-1-yn-1-yl)-1-naphthyl]methyl}amino)propyl]phosphonic acid;
- 2-({[4-(6-phenylhexyl)-1-naphthyl]methyl}amino)ethanol;
- 2-({[4-(6-phenylhexyl)-1-naphthyl]methyl}amino)ethyl dihydrogen phosphate;
- [3-({[4-(6-phenylhexyl)-1-naphthyl]methyl}amino)propyl]phosphonic acid;
- {3-[({4-[6-(3-methoxyphenyl)hex-1-yn-1-yl]-1-naphthyl}methyl)amino]propyl}phosphonic acid;
- 2-[({4-[6-(3-methoxyphenyl)hex-1-yn-1-yl]-1-naphthyl}methyl)amino]ethyl dihydrogen phosphate;
- {3-[({4-[6-(3-methoxyphenyl)hexyl]-1-naphthyl}methyl)amino]propyl}phosphonic acid;
- 2-[({4-[6-(3-methoxyphenyl)hexyl]-1-naphthyl}methyl)amino]ethanol; and
- 2-[({4-[6-(3-methoxyphenyl)hexyl]-1-naphthyl}methyl)amino]ethyl dihydrogen phosphate.

* * * * *

UNITED STATES PATENT AND TRADEMARK OFFICE
CERTIFICATE OF CORRECTION

PATENT NO. : 8,658,623 B2
APPLICATION NO. : 13/943166
DATED : February 25, 2014
INVENTOR(S) : Janet A. Takeuchi et al.

It is certified that error appears in the above-identified patent and that said Letters Patent is hereby corrected as shown below:

On the title page, item (56), under "Other Publications", in column 2, line 2, delete "Sterochemistry," and insert -- Stereochemistry, --, therefor.

In the Specification

Column 1, line 26, delete "Sphingosine-1 phosphate" and insert -- Sphingosine-1-phosphate --, therefor.

Column 9, line 66, delete "is," and insert -- is --, therefor.

Column 12, line 31, delete "Stahal&" and insert -- Stahl & --, therefor.

Column 12, line 32, delete "Chemica" and insert -- Chimica --, therefor.

Column 12, line 40, delete "Stahal&" and insert -- Stahl & --, therefor.

Column 12, line 41, delete "Chemica" and insert -- Chimica --, therefor.

Column 13, line 27, delete "antoimmune" and insert -- autoimmune --, therefor.

Column 13, line 28, delete "dermititis," and insert -- dermatitis, --, therefor.

Column 14, lines 11-12, delete "antoimmune" and insert -- autoimmune --, therefor.

Column 14, line 13, delete "dermititis," and insert -- dermatitis, --, therefor.

Column 16, line 24, delete "and or" and insert -- and/or --, therefor.

Column 17, line 50, delete "aldhyde" and insert -- aldehyde --, therefor.

Column 19, line 7, delete "diasteroisomeric" and insert -- diastereoisomeric --, therefor.

Column 28, line 24, delete "3H)" and insert -- 3H). --, therefor.

Columns 35-36, lines 25-26 (Table 3), delete "3.48-101 3.50" and insert -- 3.48-3.50 --, therefor.

Column 41, line 32, delete "dithitothreitol" and insert -- dithiothreitol --, therefor.

Signed and Sealed this
Twenty-seventh Day of May, 2014

Michelle K. Lee
*Deputy Director of the United States Patent and Trademark Office*

CERTIFICATE OF CORRECTION (continued)
U.S. Pat. No. 8,658,623 B2

Column 41, line 36, delete "5'-adenylylimmidodiphosphate" and insert -- 5'-adenylylimidodiphosphate --, therefor.

In the Claims

Column 49, line 57, in claim 7, delete "is," and insert -- is --, therefor.